(12) United States Patent
Shaw et al.

(10) Patent No.: US 10,092,735 B2
(45) Date of Patent: Oct. 9, 2018

(54) THERAPEUTIC DELIVERY DEVICE

(71) Applicants: Matthew Q. Shaw, Carmel, IN (US);
Robert F. Wallace, Fort Myers, FL (US)

(72) Inventors: Matthew Q. Shaw, Carmel, IN (US);
Robert F. Wallace, Fort Myers, FL (US)

(*) Notice: Subject to any disclaimer, the term of this patent is extended or adjusted under 35 U.S.C. 154(b) by 832 days.

(21) Appl. No.: 14/511,077

(22) Filed: Oct. 9, 2014

(65) Prior Publication Data

US 2015/0100019 A1    Apr. 9, 2015

Related U.S. Application Data

(60) Provisional application No. 61/888,581, filed on Oct. 9, 2013.

(51) Int. Cl.
*A61M 31/00* (2006.01)
*A61K 9/00* (2006.01)
*A61K 9/48* (2006.01)

(52) U.S. Cl.
CPC ......... *A61M 31/002* (2013.01); *A61K 9/0024* (2013.01); *A61K 9/4808* (2013.01)

(58) Field of Classification Search
CPC .......... A61M 31/002; A61F 2250/0067; A61F 2002/072; A61F 2/92; A61L 2300/608; A61L 2300/604; A61L 2300/60
See application file for complete search history.

(56) References Cited

U.S. PATENT DOCUMENTS

| | | | |
|---|---|---|---|
| 5,989,579 A | | 11/1999 | Darougar et al. |
| 6,090,996 A | * | 7/2000 | Li ............... A61L 31/148 606/151 |
| 6,251,090 B1 | | 6/2001 | Avery et al. |
| 6,589,225 B2 | | 7/2003 | Orth et al. |
| 7,582,080 B2 | | 9/2009 | Santini et al. |
| 7,794,490 B2 | | 9/2010 | King |
| 7,824,699 B2 | | 11/2010 | Raloh et al. |
| 7,892,221 B2 | | 2/2011 | Santini, Jr. et al. |
| 2005/0283224 A1 | | 12/2005 | King |
| 2007/0207186 A1 | * | 9/2007 | Scanlon ............ A61F 2/07 424/424 |
| 2007/0282425 A1 | | 12/2007 | Kleine et al. |

OTHER PUBLICATIONS

U.S. Office Action for U.S. Appl. No. 13/481,426 dated Jan. 27, 2015.

* cited by examiner

*Primary Examiner* — Deanna K Hall
(74) *Attorney, Agent, or Firm* — Rathe Lindenbaum LLP

(57) ABSTRACT

A therapeutic delivery device comprises a layer of biodegradable material wound into a plurality of windings, the plurality of windings comprising an outermost winding defining an internal volume and winding pairs including a first winding pair and a second winding pair. A first therapeutic mass is incorporated in or on the layer the first winding pair and a second therapeutic mass is incorporated in or on the layer along the second winding pair. In one implementation, at least one volume of gas is captured within the internal volume and occupies at least 50% of the internal volume. In one implementation, the windings include perforations.

19 Claims, 16 Drawing Sheets

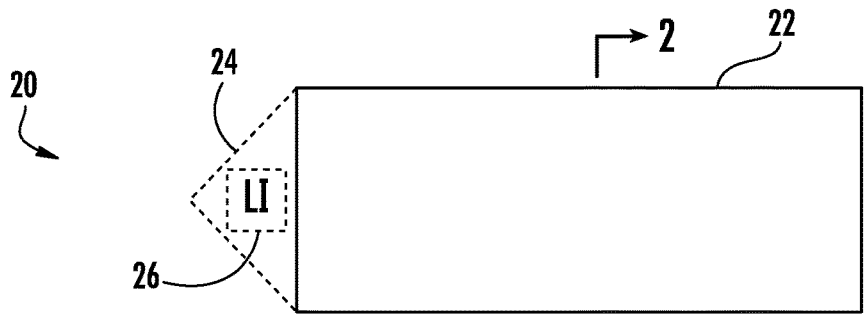
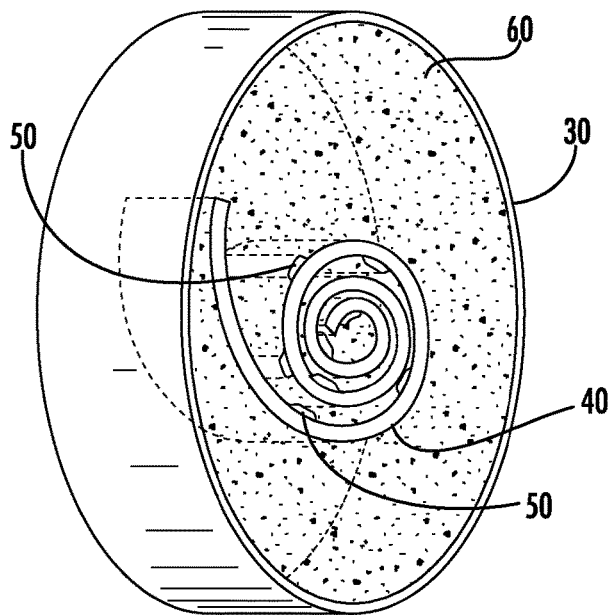
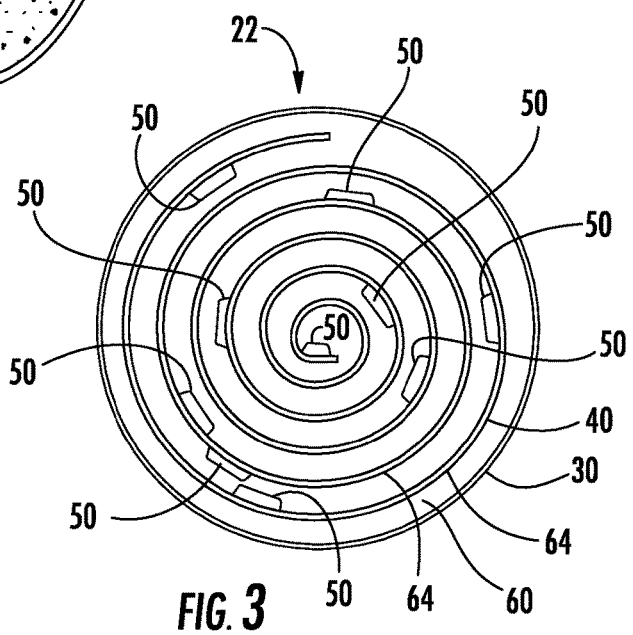

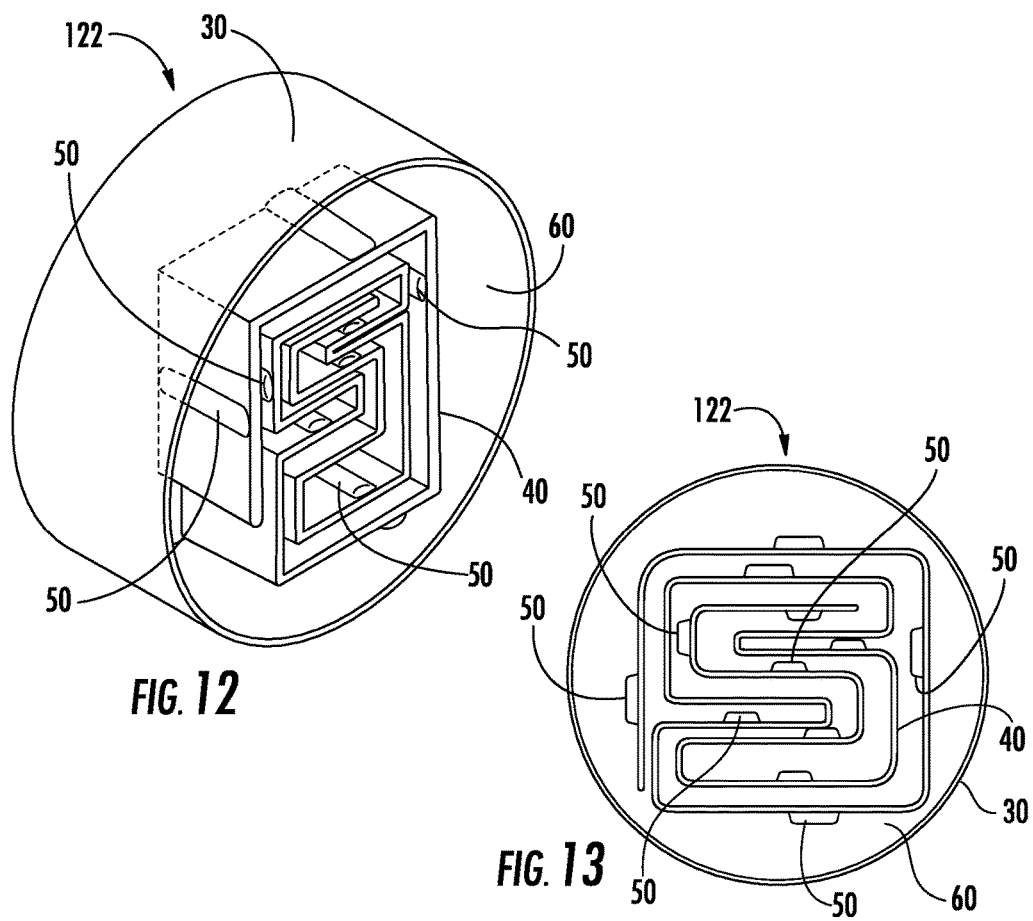
FIG. 12
FIG. 13
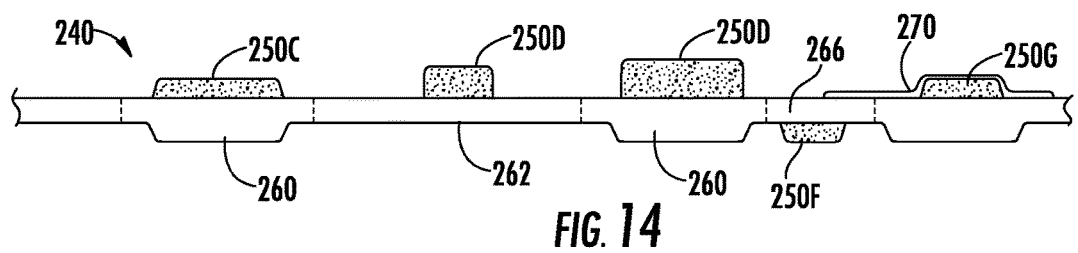
FIG. 14
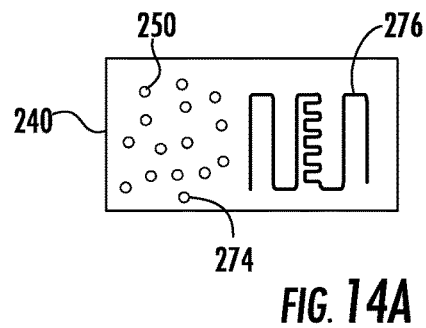
FIG. 14A

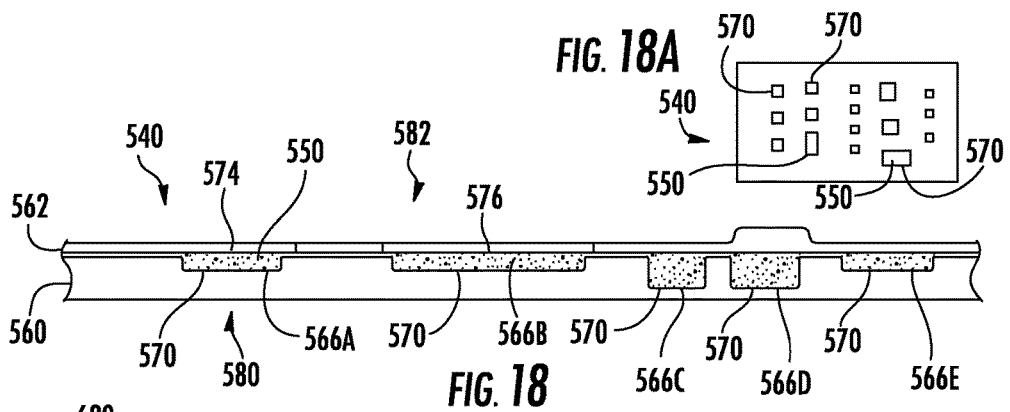
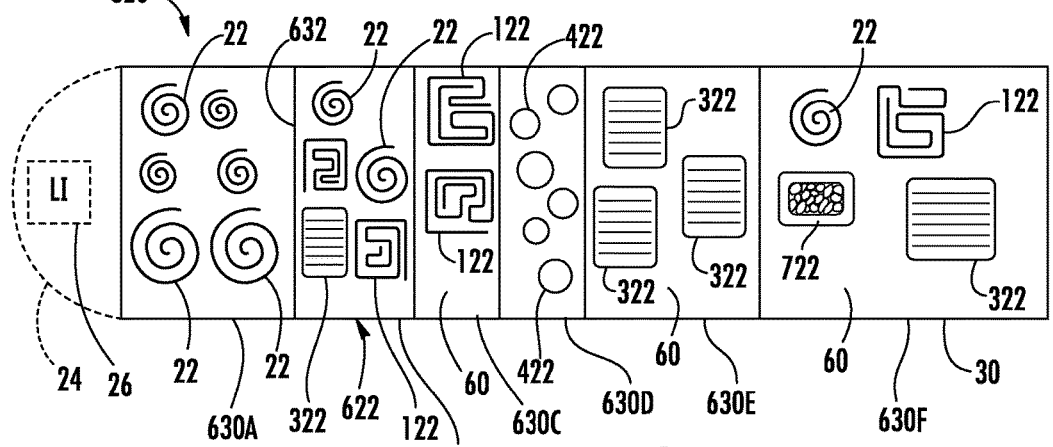
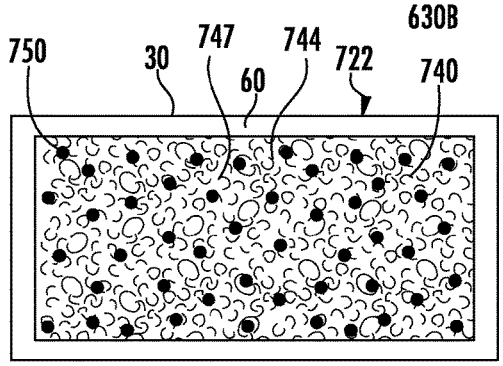
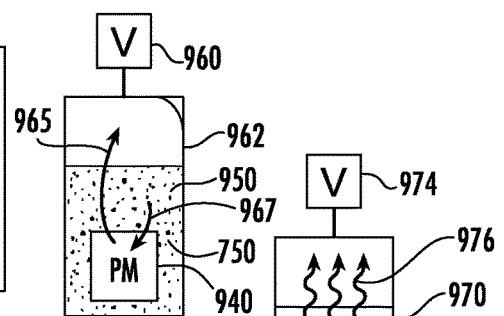
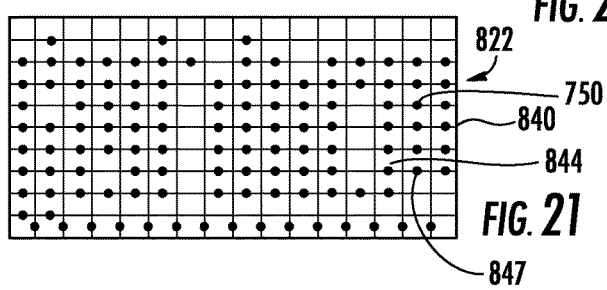
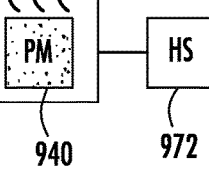

THERAPEUTIC DELIVERY DEVICE

CROSS-REFERENCE TO RELATED PATENT APPLICATIONS

The present application claims priority under 35 USC 120 from U.S. Provisional Patent Application Ser. No. 61/888,581 filed on Oct. 9, 2013 by Wallace et al. and entitled IMPLANT, the full disclosure of which is hereby incorporated by reference.

BACKGROUND

Therapeutics, vaccines, medicines and drugs (collectively referred to as therapeutics) are sometimes administered in liquid form via shots. In other circumstances, such therapeutics are delivered orally in the form of pills. In some circumstances, therapeutics are delivered via implants. Such therapeutic delivery systems and devices are often complex and difficult to manufacture or are difficult to precisely control a timed release of different therapeutics.

BRIEF DESCRIPTION OF THE DRAWINGS

FIG. 1 is a side of an example therapeutic delivery device.
FIG. 2 is a fragmentary perspective view of an example of the device of FIG. 1.
FIG. 3 is a sectional view of the device of FIG. 1 taken along line 2-2.
FIG. 12 is a perspective view of another example of the device of FIG. 1.
FIG. 13 is an end view of the device of FIG. 12.
FIG. 14 is a fragmentary sectional view of an example of a sheet and therapeutics for forming an therapeutic delivery device.
FIG. 14A is a top plan view of an example of a sheet with an example pattern of therapeutics thereon prior to being folded.
FIG. 18 is a fragmentary sectional view of another example of a sheet and therapeutic for forming a therapeutic delivery device.
FIG. 18A is a top elevational view of an example sheet with an example pattern of therapeutics thereon for forming a therapeutic delivery device.
FIG. 19 is a sectional view schematically illustrating another example of the therapeutic delivery device of FIG. 1.
FIG. 20 is a sectional view illustrating another example of the therapeutic delivery device FIG. 1.
FIG. 21 is a sectional view illustrating another example of the therapeutic delivery device of FIG. 1.
FIGS. 22 and 23 are schematic diagrams illustrating an example method for forming the therapeutic delivery device shown in FIG. 20 or FIG. 21.

DETAILED DESCRIPTION OF THE EXAMPLE EMBODIMENTS

Figure 4:
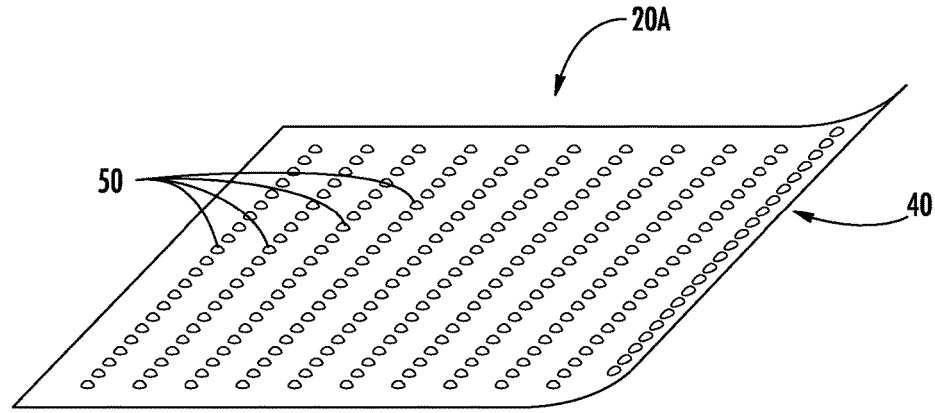
FIG. 4 is a perspective view of a biodegradable sheet having rows of therapeutics deposited thereon.

FIG. 1 is a side elevational view illustrating an example therapeutic delivery device 20 configured to be implanted via a needle into a patient, such as a person or animal, for timed release of one or more therapeutics. As will be described hereafter, device 20 delivers or releases therapeutics in a precisely controlled time fashion using a less complex and more easily manufactured delivery structure. As shown by FIG. 1, device 20 comprises an elongated main body 22 containing such therapeutics. Although illustrated as an elongated cylinder, in other implementations, body 22 may comprise an elongated polygon, an elongated brick (prism), ellipsoid or a sphere. In other implementations, body 22 may have other 3D shapes. In one implementation, body 22 is configured to be implanted within a human anatomy, having a maximum length of 4 cm and a maximum width of 0.5 cm. In other implementations, body 22 may have other dimensions.

As shown in broken lines, in some implementations, device 20 may additionally include a pointed or rounded tip 24 to facilitate easier penetration into tissue with reduced damage to body tissue. In one implementation, tip 24 may include a location identifier 26 comprise a material facilitating identification of a location of therapeutic delivery device 20. For example, in one implementation, location identifier 26 may comprise a radioactive material, a radio opaque material or a sonogenic material, or assume a sonogenic shape, to allow real time precision placement, or post placement confirmation/identification. In other implementations, location identifier 26 may comprise other sensing materials. In yet other implementations, tip 24 may be omitted.

FIGS. 2 and 3 illustrate one example of body 22 of therapeutic delivery device 20. In the example illustrated in FIGS. 2 and 3, body 22 comprises outer shell 30, sheet 40 and therapeutic masses 50. Outer shell 30 comprises a wall of biodegradable material that encapsulates or surrounds sheet 40 and therapeutic masses 50. Examples of biodegradable materials from which outer shell 30 is formed or from which other biodegradable components of body 22 or device 20 are formed, such as sheet 40, include but are not limited to, a cellulose, or variants thereof, glycolic acid derived membranes or other materials forms, or their combinations, with characteristics such that the materials are biodegradable naturally and completely in the host body The degradation may be time controlled by two factors: the nature and amount of the material, and the final 3D configuration rendered via different wrapping, folding, spacing, differential chambering. Other industrial processing, such as ink jet like position, drying, vacuum, sponge absorption, may be utilized as well. The therapeutic will be pre-positioned in the 2D stage as different density and pattern, when wrapped or folded (or other method illustrated below) into a 3D configuration, such that its release profile will be tailored to its pharmacological goal: extended, time controlled, concentration range bound.

In one implementation, outer shell 30 contacts outermost surfaces of sheet 40. In other implementations, outer shell 30 may be formed by or may contain an inner core material 60 that extends between outer surfaces of shell 30 and sheet 40. In some implementations, the core material may fill spaces between the different layers formed by sheet 40. In one implementation, outer shell 30 is formed from a material or is coated with a material configured to inhibit or stop bleeding during its placement.

Sheet 40 comprises a single continuous panel of biodegradable material supporting or carrying therapeutic masses 50. The therapeutic masses 50 may be evenly distributed throughout and within the sheet 40 or may be deposited on one side or both sides of the sheet. For easy understanding, FIGS. 2 and 3 illustrate the patches of therapeutic masses 50 deposited in distinct locations on the surface of sheet 40. In the example shown in FIG. 2, sheet 40 is wrapped such that the single panel or sheet 40 forms a plurality of spaced biodegradable layers 64 separating different therapeutic masses 50. For purposes of this disclosure, the term "wrapped" means that a single sheet is bent, wound or otherwise shaped such that portions of sheet 50 face one another or overlap one another. In the example illustrated, sheet 40 is illustrated as being helically or spirally wound. In other words, sheet 40 comprises a plane curve cross-section generated by point moving around a fixed point while constantly receding from or approaching the fixed point to form a helix. Although illustrated as being spirally wound as a cylinder having a circular cross-section, concentric about a centerline or axis, in other implementations, sheet 40 may be spirally wound by one or more axes so as to have an elliptical cross-section or multi-lobed cross-section. In other implementations, sheet 40 may be "wrapped" in other fashions.

Figure 24:
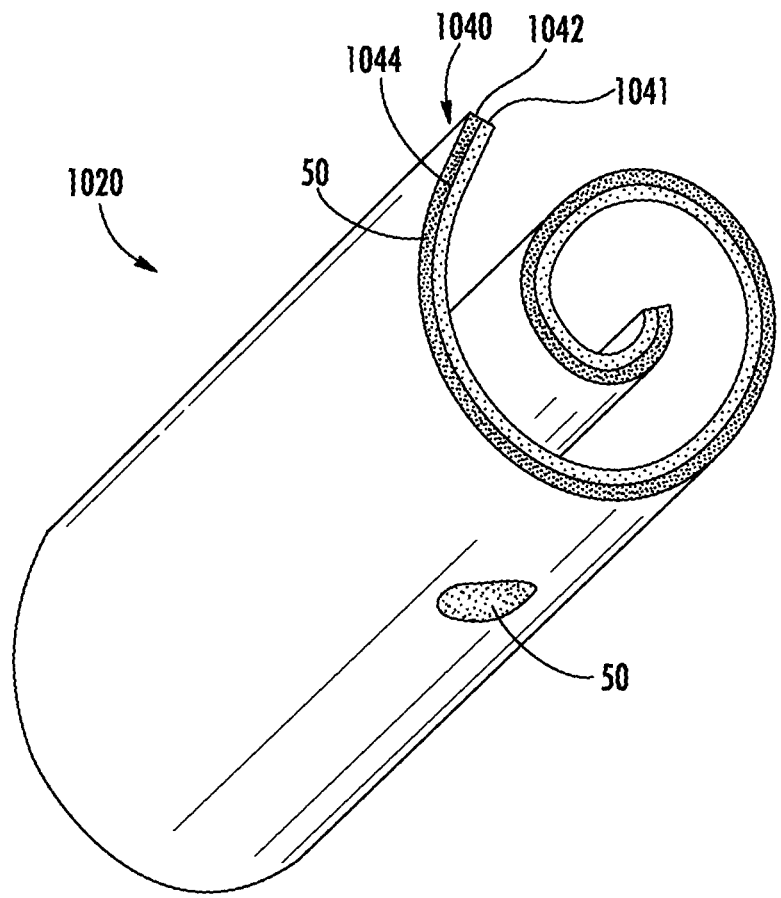
FIG. 24 is a perspective view of an example biodegradable sheet.

Although sheet 40 is illustrated as a single layer of material or materials that is wrapped to form the layer 64, in each of the examples described, sheet 40 may specifically comprise a combination of two or more biodegradable membranes stacked or laminated together. FIG. 24 illustrates an implant 1020 comprising an example sheet 1040 which may be wrapped or stacked to form the multiple layers 64 described above. Sheet 1040 comprises a stack of two or more sub layers. In the example illustrated, sheet 1040 comprises sub layers 1041 and 1042. In one implementation, sublayer 1041 comprises a hydrophobic layer (such as PLGA described below) while sublayer 1041 comprises a hydrophilic layer, such as a cellulose layer. In one implementation, one of layers 1041, 1042 may be hydrophilic on the other of layers is lipidphilic. In one implementation, sub layers 1041 and 1042 have different chemical or physical properties or characteristics character (hydrophilic, lipidphilic), or physical character (elasticity, glass melting temperature), or combination of such (hydrophilic membrane stack on lipidphilic sublayers. In some implementations, one or both of sub layers 1041, 1042 may have varying thicknesses or varying properties across the individual sublayer itself. For example, portions of one or both of sub layers 1041, 1042 may be thinner at one end of the sheet 1040 and thicker at the other end of sheet 1040 such that the outermost layer 64 are thinner while the innermost layers 64 are thicker to achieve a burst of therapeutic release at the onset. In one implementation, one or both of layers 1041, 1042 may have central regions or craters of reduced thickness or mounds of increased thickness to vary the time release of therapeutics.

In one implementation, the therapeutic mass 50 is a deposited upon one or both of the interfaces 1044 between the two layers 1041, 1042 so as to be sandwiched between the layers. In another implementation, the therapeutic mass 50 is embedded in one or both of such layers. For example, the therapeutic mass 50 may be injected after such layers are formed. In another implementation, the therapeutic mass may be homogenously mixed with the ingredients or particles that form one or both of layers 1041, 1042 prior to the actual forming of the layers with the mixture. In one implementation, one sub-layer 1041, 1042 may have a different amount of the therapeutic mask as compared to the other sub-layer 1041, 1042. In one implementation, therapeutic mass 50 is evenly distributed, or evenly embedded as part of layers 1041, 1042. In yet other implementations, therapeutic mass 50 may be non-uniformly or unevenly distributed across one or both of layers 1041, 1042.

Because sheet 40 is wrapped, outermost therapeutic masses 50 on sheet 40 may be exposed and therefore released at times before innermost therapeutic masses 50 on sheet 40. As a result, the time at which a therapeutic is exposed and thereby delivered or released into a body may be predefined or controlled based upon the relative inner or outer positioning of the therapeutic mass 50 on the various windings of sheet 40. For example, therapeutic mass 50G will be exposed and thereby released at a time much later than the release of therapeutic mass 50A.

Therapeutic masses 50 comprise medicinal materials supported or carried by sheet 40. Examples of therapeutic masses 50 include, but are not limited to, pharmaceuticals (chemotherapy agents, antibiotics, antiviral agents, antihypertension agents, vassodilatation agents, vasoconstriction agents, local anesthetics, NSAIDA, steroids, psychotropic agents, neurotropic agents), proteins (including antibodies, interferons and hormones, peptides (interleukins, RNA's) osteogenic and osteolytic agents, genetic altering agents and livings cell (including stem cells). Such therapeutics may be solid, semi-liquid or liquid.

In one implementation, each of therapeutic masses 50 may constitute the same therapeutic formulation in generally the same doses. In other implementations, some of therapeutic masses 50 may be different formulations or different doses of the same therapeutic formulation. For example, an outer therapeutic mass 50 may comprise a first type of therapeutic while and inner therapeutic mass 50 may comprise a different type of therapeutic. In one implementation, multiple therapeutic masses may be applied along sheet 40 in a desired sequence such that the different therapeutic masses are released in a sequenced manner. In the example illustrated in FIG. 2, therapeutic masses 50 are located on both sides of sheet 40. In other implementations, therapeutic masses 50 may be located on only one side of sheet 40.

Figure 5:
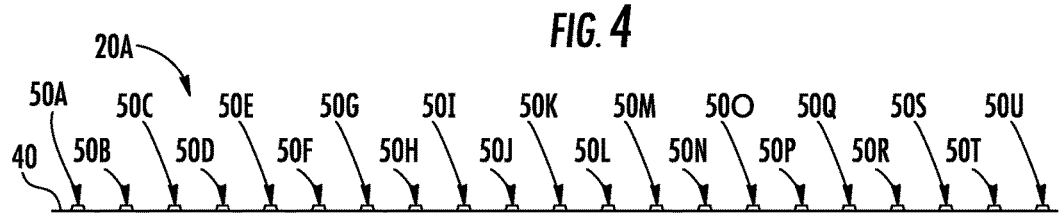
FIG. 5 is an end view of the biodegradable sheet with rows of therapeutics of FIG. 4.
Figure 6:
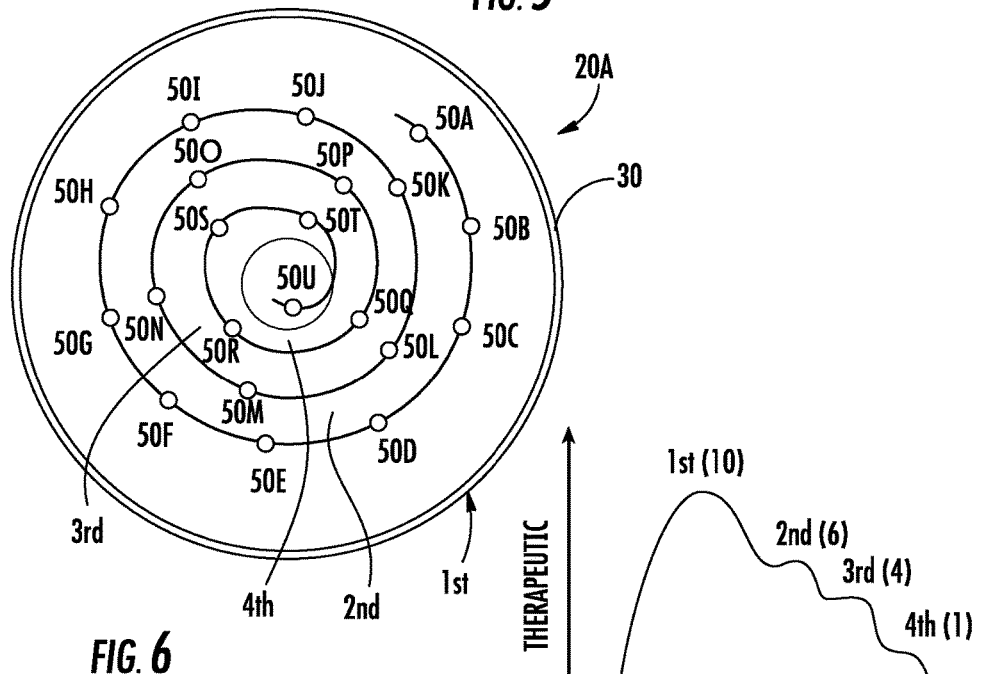
FIG. 6 is an end view of the biodegradable sheet of FIG. 5 spirally wound and enclosed within a shell to form therapeutic delivery device.
Figure 7:
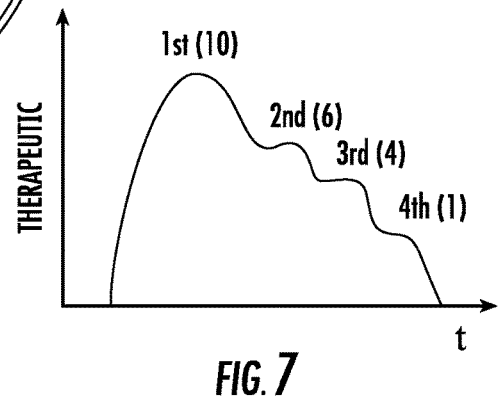
FIG. 7 is a graph illustrating the timed release of therapeutics from the therapeutic delivery device of FIG. 6.

FIGS. 4-6 illustrate one example method of forming therapeutic delivery device 20A, a particular example of therapeutic delivery device 20. Therapeutic delivery device 20A is identical to therapeutic delivery device 20 except that therapeutic delivery device 20A has the specific therapeutic release profile as shown in FIG. 7). As shown by FIGS. 4 and 5, while sheet 40 is substantially flat, therapeutic masses 50A-50U are deposited upon sheet 40. In the example illustrated, therapeutic masses 50A-50J each comprise a row of multiple spaced spots of therapeutics or continuous line of therapeutics, wherein the rows are evenly spaced across sheet 40. As shown by FIG. 6, after deposition or application of therapeutic masses 50A-50U, sheet 40 is wrapped (spirally wound in the illustrated example).

FIG. 7 is a graph illustrating the release of therapeutics over time with implant 20A. As shown by FIG. 6, the outermost winding has a largest circumference and therefore has the largest number of rows of therapeutics. The innermost winding has the smallest circumferential length, having the fewest number of rows of therapeutics. In the example illustrated, the outermost winding has 10 rows of therapeutics, the next inner winding has 6 rows of therapeutics, the next inward winding has 4 rows of therapeutics and the innermost winding or portion of sheet 40 has just 1 row of therapeutics. As implant 20A and the layers biodegradable material between the various windings breaks down, the therapeutics on the windings are sequentially exposed, sequentially releasing therapeutics, beginning with the outermost winding and finishing with the innermost winding. As shown by FIG. 7, implant 20A achieves a timed release of therapeutics wherein the largest amount of therapeutics is initially released and subsequent release of type UNIX are stepwise reduced over time.

Figure 8:
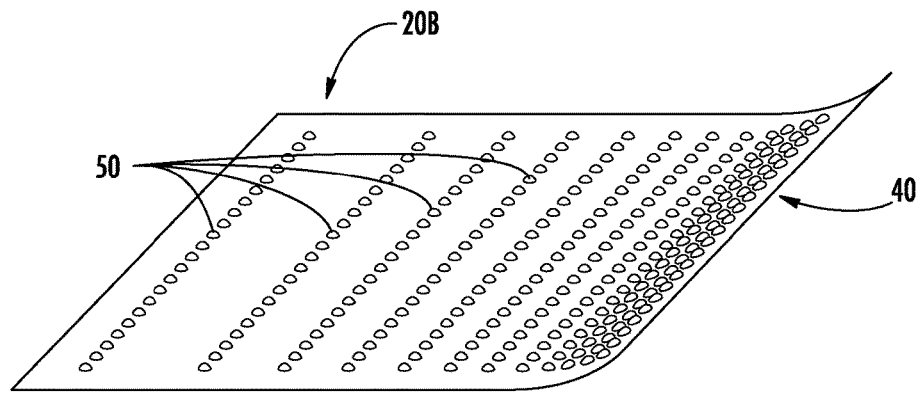
FIG. 8 is a perspective view of another biodegradable sheet having rows of therapeutics deposited thereon.
Figure 9:
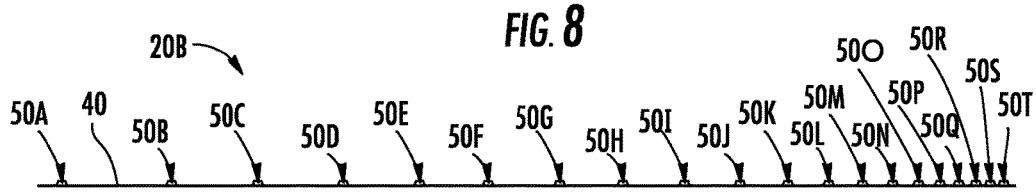
FIG. 9 is an end view of the biodegradable sheet with rows of therapeutics of FIG. 8.
Figure 10:
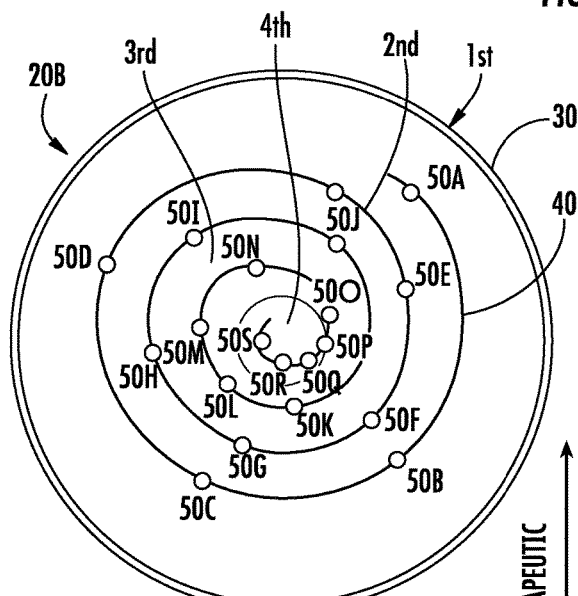
FIG. 10 is an end view of the biodegradable sheet of FIG. 5 spirally wound and enclosed within a shell to form a therapeutic delivery device.
Figure 11:
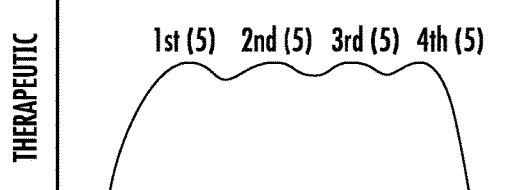
FIG. 11 is a graph illustrating the timed release of therapeutics from the therapeutic delivery device of FIG. 10.

FIGS. 8-10 illustrate another example method of forming an therapeutic delivery device 20B, a particular example of therapeutic delivery device 20. Therapeutic delivery device 20B is identical to therapeutic delivery device 20 except that therapeutic delivery device 20B has the specific therapeutic release profile as shown in FIG. 11). As shown by FIGS. 8 and 9, while sheet 40 is substantially flat, therapeutic masses 50A-50T are deposited upon sheet 40. In one implementation, such therapeutic masses 50 are applied or deposited upon sheet 40 while sheet 40 is substantially flat, wherein after deposition of such therapeutic masses 50, sheet 40 is wrapped. In the example illustrated, therapeutic masses 50A-50T each comprise a row of multiple spaced spots of therapeutics or continuous line of therapeutics, wherein the rows are unevenly spaced across sheet 40. As shown by FIG. 10, after deposition or application of therapeutic masses 50A-50T, sheet 40 is wrapped (spirally wound in the illustrated example).

FIG. 11 is a graph illustrating the release of therapeutics over time with implant 20B. As shown by FIG. 9, therapeutic masses 50A-50T are non-uniformly deposited along sheet 40. In the example illustrated, therapeutic masses 50A-50T are non-uniformly or unevenly spaced such that each winding carries approximately the same number of rows of therapeutics. In the example illustrated, the outermost winding has a largest circumference and therefore has the largest spacing between rows of therapeutics. The innermost windings have smaller circumferences and smaller length, having the smallest spacing between rows of therapeutics. In the example illustrated, each of the windings or layers has five rows of therapeutics. In other implementations, the windings or layers may have a greater or fewer number of such rows. As implant 20B breaks down, the windings are sequentially exposed, sequentially releasing therapeutics, beginning with the outermost winding and finishing with the innermost winding. As shown by FIG. 11, implant 20B achieves a timed release of therapeutics wherein the amount of therapeutics is substantially constant over time (the fences same model therapeutics is released upon exposure of each of the layers or windings. As shown by implant 20A and implant 20B, the timing of therapeutic release as well as the amount of therapeutics provided at each therapeutic release may be varied and controlled by controlling the number of windings, the spacing of the windings and the spacing of the rows or other deposits of therapeutics along sheet 40 and amongst the layers.

In one implementation, therapeutic masses 50 may be printed upon sheet 40 such as with a drop-on-demand inkjet print head. As a result, the amount and the location of each of therapeutic mass 50 may be precisely and accurately controlled. In other implementations, therapeutic masses 50 may be applied to one or both sides of sheet 40 using other techniques.

Once the therapeutic masses 50 have been applied to sheet 40, sheet 40 is wrapped. In other implementations, the therapeutic masses 50 upon sheet 40 may be sealed in place upon sheet 40 by applying one or more overcoats or films over sheet 40 to encapsulate the applied therapeutic masses 50. Such an overcoat or sealing layer may comprise a thin membrane of biodegradable material. After such sealing or lamination, layer 40 may be folded.

FIGS. 12 and 13 illustrate body 122, another example of body 22 of implant 20. Body 122 is similar to body 22 except that sheet 40 which therapeutic masses 50 is wrapped in a different manner. Instead of being spirally wound as sheet 40 as in body 22, sheet 40 is folded. In contrast to being spirally wound wherein sheet 40 is always extending inwardly or outwardly circumferentially about a centerline or axis, sheet 40 in body 122 is wrapped wherein sheet 40 extends in opposite directions at times. Although illustrated as being folded in the form of a square or rectangular cross-sectional shape, in other implementations, sheet 40 may be wrapped or folded with other folding patterns so as to have other cross-sectional shapes. This 3D configuration also started with a 2D membrane shown in FIG. 3A, with prepositioned 50. Then the membrane is folded multiple times as illustrated to its final 3D construction with the therapeutic release profile being changeable or controlled based on the different pattern of therapeutic masses 50 on the 2D membrane or sheet 40.

In each of the examples shown in FIGS. 2 to 12, the timed release of therapeutic masses 50 may be adjusted or controlled by adjusting factors such as how tight sheet 40 is wrapped or wound, the number of wraps or windings and the folding pattern (with respect to the example in FIG. 3). Identical sheets 40 having an identical patterns of deposit therapeutics may be provided with different time release characteristics by simply adjusting any of the aforementioned factors. In other implementations, the timed release of therapeutics (the timing at which therapeutics are released) may be adjusted further by adjusting the pattern at which therapeutic masses 50 are applied to sheet 40 prior to such wrapping.

In one implementation, the inner core material 60 does not fill or occupy the space between the wraps or windings, but only extends between the outermost winding and shell 30. In such an implementation, the wraps or windings capture gas, such as air, between the windings and within the internal volume of the implant of FIGS. 2-12. Such gas pockets or gas layers reduce the rate at which therapeutic masses 50 are released. In one implementation, the outermost winding defines an internal volume, wherein the one of more sheets are loosely wall or wrapped such that the gas or air captured within the internal volume occupies at least 50% of the internal volume. In one implementation, the one of more sheets 40 which are loosely wrapped or wound and any therapeutics constitute less than or equal to 20% of the total volume of the implant with the gas or air constituting the remaining percentage of the total volume. In yet another implementation, air or gas occupies the volume or space between some of the winding pairs while inner core material 60 (or another biodegradable filler material) occupies the volume or space between other winding pairs. In such an implementation, selectively filling the volume or space between different winding pairs with air/gas or with one or more other biodegradable filler materials facilitates greater control over the different times at which therapeutics along different winding pairs become exposed and are released.

Figure 25:
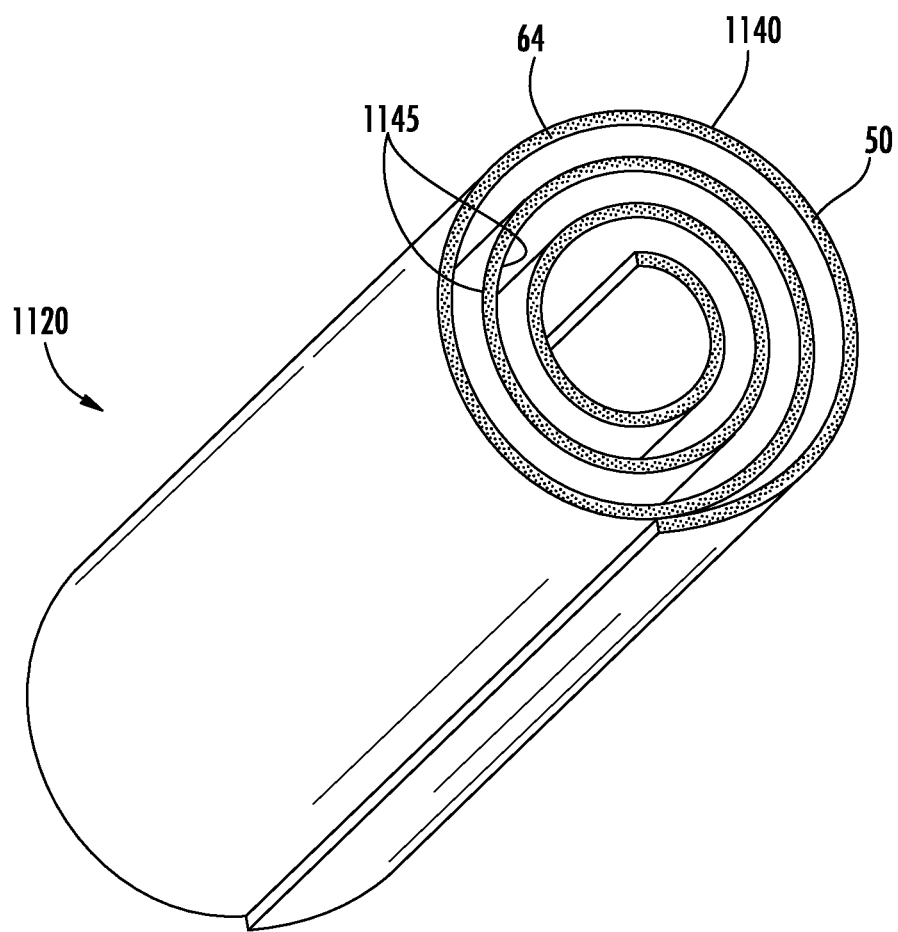
FIG. 25 is a perspective view of an example therapeutic implant.

FIG. 25 illustrates an example solid therapeutic implantable device (STID) for solid tumors, such as breast and prostate cancer treatment in accordance with the above mentioned principles. The active antitumor agent is Doxorubicin, a well documented, still widely used anthracycline antibiotic. It has chemotherapy effect against a variety of human cancer, breast, prostate etc, mainly by damaging cellular DNA, thus killing actively growing tumor cells, as well as normal host cells. Unfortunately, it has two systemic side effects that limit its usage, myelosuppression and dose-cumulative cardiotoxicity.

The solid therapeutic implantable device (STID) 1120 containing a therapeutic mass 1150 Doxarubicin will be named STID-Dox-PLGA85/15 for future discussion. The biodegradable membrane serving as sheet 1140 is poly-lactide-glycolide copolymer (PLGA), with the ratio of lactide:glycolide of 85; 15, and the average modecular weight of 100 D. This polymer is one of the many varieties of poly-lactide-glycolide copolymer, widely available commercially, FDA approved for implantation for human and animals.

Briefly the STID-Dox-PLGA85/15 is constructed as follows: 55 mg of the PLGA85/15 and 2 mg of Doxarubicin was dissolved in 1 ml of chloroform. The solution is then spread on a flat surface in a circle about 1.5 cm diameter, and air dried in a laminar flow hood. The dried membrane is then rolled 3 times as showed in FIG. 26. 3 times meaning three 360 degree roll, the resulting cylinder has 3 membranes in every radius direction. The excess is trimmed, and the resulting STID-Dox-PLGA85/15 has a diameter about 800 um and length about 8 mm. The space between the layers 64 is filled with air. In other implementations, such space may be filled with body fluid or other liquid.

The timed release of therapeutic mass 50 by implant 1120 exhibits two characteristics. First, the interlayer in the construct is either filled with air or local tissue fluid depending how tight the wrapping seal. The therapeutics from the inside layers has to diffuse through change of medium multiple times before it reaches to the outside of the implant. Each change of medium is an interface 1145 of different material, in this example total 6 interfaces were illustrated. In other implementations, a greater or fewer of such interfaces may be provided depending upon the number of wraps or the number of layers in a stack. The time for a solute to diffuse across an interface of two different materials is a measurable character. Thus, the plurality of the biodegradable layers contributes to a new variable, rather than the pure biodegradable matrix material itself, in terms of diffusion rate of the therapeutics. Generally the diffusion rate will be slower, proportional to the number of layers/windings (more specifically, the number of interfaces).

Second, the outer layers will protect the therapeutics in the inside layer, especially in implementations where the interlayer space is a thin air or other gas. In one implementation, sheet 1140 is loosely wound such that implant 1120 has a volume of captured air or gas that occupies at least 50% of the internal volume and nominally at least 75% of the internal volume. In the example described, sheet 1140 occupies between 15% and 20% of the total internal volume of implant 1120 with the remaining volume occupied by air. For the doxorubicin in this construct, 3 weeks inside an animal body about 37 C, its efficacy is still preserved.

STID-Dox-PLGA85/15 has demonstrated a long term antitumor activity, with good safety profile, decreased toxicity, making it a viable candidate chemotherapy device for varieties of human tumors, breast, prostate in particular.

FIG. 14 is a sectional view illustrating sheet 240 and therapeutic masses 250, an example implementation of sheet 40 and therapeutic masses 50, respectively, prior to wrapping. FIG. 14A is a top plan view of sheet 240 and therapeutic masses 250 prior to wrapping. Therapeutic masses 250 are the same as therapeutic masses 50 but for the varying of the density and patterning as will be described hereafter. As shown by FIG. 14, in addition to varying or controlling the release of therapeutics by varying wrapping characteristics of sheet 240, such release may also be adjusted are controlled by varying characteristics of sheet 240 itself or characteristics of the applied therapeutic masses 250.

As shown by FIG. 14, one technique for varying or controlling the release of therapeutic masses 250 is to vary a thickness of sheet 240 underlying therapeutic mass 250. In the example illustrated, sheet 240 is thicker in region 260 underlying therapeutic mass 250C than region 262 underlying therapeutic mass 250D. The thicker region 260 may result in therapeutic mass 250C being released are exposed at a later time as compared to an implementation where therapeutic mass 250C were deposited upon a region having a thickness of region 262.

As shown by FIG. 14, another technique for varying a controlling release of therapeutic masses 250 with device 22 is to vary the material or materials forming different portions of sheet 240. For example, region 262 underlying therapeutic mass 250D may form from a first biodegradable material which degrades at a much slower rate as compared to the biodegradable material forming region 266 supporting therapeutic mass 250F. As a result, even portions of layer 250 having the same thickness, may have different therapeutic release characteristics due to the different materials forming the different portions of sheet 240. In some implementations, both the material forming different regions of sheet 240 as well as the thicknesses of such different regions may be varied or controlled to vary the timing at which therapeutic masses 250 are delivered.

As shown by FIG. 14, another technique for varying or controlling release of therapeutic masses 250 with device 22 (or device 122) is to vary the exposed outer surface area of the therapeutic mass 250 on sheet 240. For example, a same amount of therapeutic mass 250 spread over a larger area sheet 240 may be more quickly exposed, released and absorbed (or dissolved) as compared to the same amount of therapeutic mass 250 deposited so as to have a much smaller outer or exposed surface area.

FIG. 14 illustrates yet another example method by which release of therapeutic masses 250 may be adjusted. As shown by FIG. 14, once therapeutic masses 250 have been deposited upon sheet 240, such deposited therapeutics may be coated (such as with a laminate, a spray or the like) with an overlying biodegradable layer 270. The thickness of layer 270 may be varied to further adjust the timing of which a therapeutic (such as therapeutic mass 250G in the illustration) is released. Different coatings 270 may be formed from different materials as well to provide different release characteristics. In some implementations, coatings 270 may completely seal or encapsulate the particular therapeutic mass 250. In other implementations, coatings 270 may only partially cover the underlying therapeutic mass 250, wherein the coatings 2 study will still impact the rate at which the therapeutic mass 250 is released.

FIGS. 14 and 14A illustrate control over delivery of therapeutic masses 250 based upon deposition of therapeutic masses 250 upon sheet 240. As shown by FIG. 14, different regions of sheet 240 may have deposited thereon different volumes or amounts of therapeutics in different shapes or surface area extends. As shown by FIG. 14A, the release or delivery of therapeutic masses 250 may further be controlled across a length of body 22 (or body 122) by controlling the patterning of the therapeutic upon sheet 240. For example, therapeutic masses 250 may be applied to sheet 240 at spaced locations in the form of spots, patches, drops and the like (identified with reference numeral 274). Alternatively, therapeutic masses 250 may be applied sheet 240 in a continuous fashion along the surface of sheet 240. For example, therapeutic masses 250 may be applied, printed or deposited in a continuous line or series of line segments having different patterns depending upon the timing at which therapeutics are to be delivered. When the delivery of therapeutic mass 250 is to be more frequent or more intense, the particular therapeutic may be applied to an appropriate portion of sheet 240 at a high density of spots or a high density of line segments 276. Likewise, when the delivery of therapeutic masses 250 is to be more spaced out or less frequent, the spacing between such spots 254 or the density of line segments 276 on sheet 240 may be reduced. Use of drop-on-demand inkjet printing may facilitate accurate and precise control over deposition of therapeutic masses 250 upon sheet 240 with the desired spacings, densities or patterns. In some implementations, therapeutic masses 250 may be applied by being spread upon the surface of sheet 240.

Figure 15:
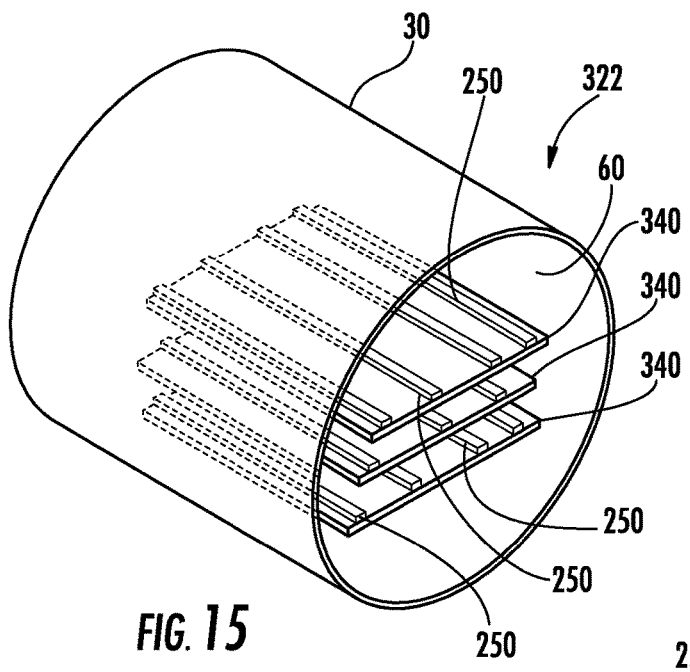
FIG. 15 is a fragmentary perspective view of another example of the device of FIG. 1.
Figure 16:
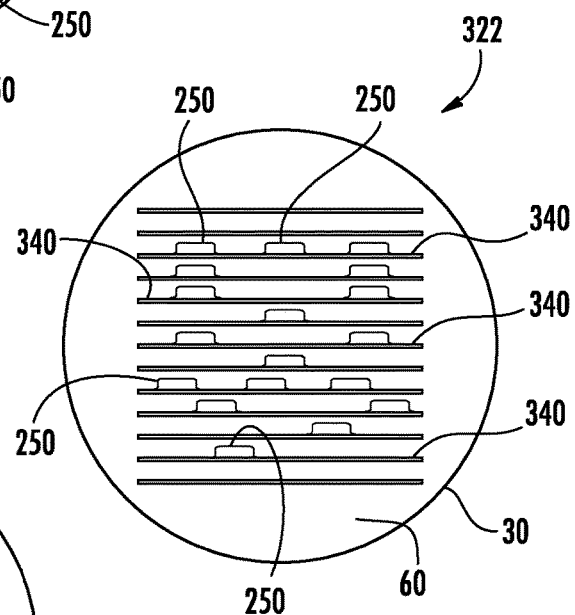
FIG. 16 is an end view of the device of FIG. 15.

FIGS. 15 and 16 illustrate body 322, another example implementation of body 22 of therapeutic delivery device 20. Body 322 is similar to body 22 except that instead of wrapping sheet 240 (or sheet 40), sheet 240 (or sheet 40) is severed or cut into a plurality of smaller sheets 340, some of which carry therapeutic masses 250. The multiple sheets 340 are then stacked such that the multiple sheets 340 form a plurality of spaced biodegradable layers between therapeutic masses 250. As shown in FIG. 5, some of layers 340 may omit therapeutic masses 250. As shown by FIG. 5, some layers 340 may include a single patch, spot or segment of a therapeutic mass 250 while other of layers 340 include multiple patches, spots or line segments of a same or different therapeutic mass 250. Although such sheets 340 may be formed by applying therapeutic mass 250 across a single continuous sheet 240 and then severing the sheet into smaller sheets 340, in other implementations, sheets 340 may be formed separately or may be cut from a larger sheet into smaller sheets 340, prior to the application of therapeutic masses 250.

Figure 17:
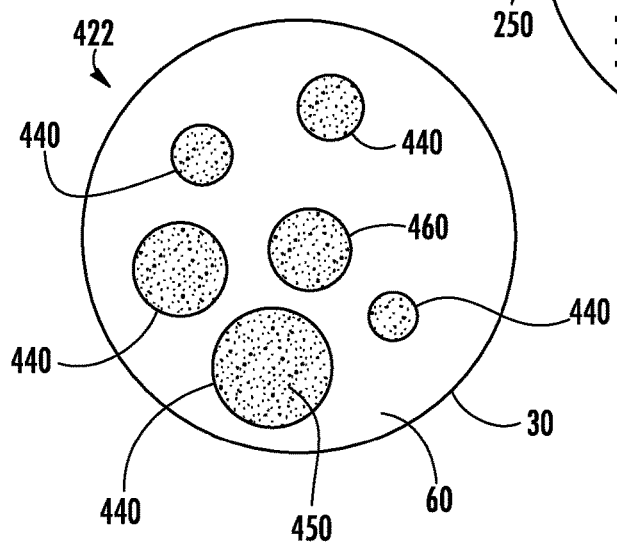
FIG. 17 is a sectional view of another example of the device of FIG. 1 taken along line 2-2.

FIG. 17 is a cross-sectional view illustrating body 422, another example implementation of body 22 of therapeutic delivery device 20. As shown by FIG. 17, body 422 comprises biodegradable outer shell 30 encapsulating our surrounding a plurality of spaced spheres 440, wherein each sphere 440 contains therapeutic particles 450 or therapeutics in other forms. In one implementation, spheres 440 are encapsulated are surrounded by core material 60 (described above). Each sphere 440 has opposite side walls which serve as biodegradable layers separating the therapeutic masses 450 within the different spheres 440. As shown by FIG. 17, the size and number of such spheres 440 and the amount or type of therapeutics contained within such spheres may be varied. For example, one sphere 440 may contain a first type of therapeutic while another sphere 440 contains a different type of therapeutic. In one implementation, different spheres 440 may have outer walls of different thicknesses or may have different inner core materials 460 encapsulating the inner therapeutic particles 450, wherein the different outer wall thicknesses are the different inner core materials for 60 provide different release times or release rates for the contained therapeutic masses 450.

FIG. 18 is a sectional view illustrating sheet 540 and therapeutic masses 550, an example implementation of sheet 40 and therapeutic masses 50, respectively, prior to wrapping. FIG. 18A is a top plan view of sheet 540 and therapeutic masses 550 illustrating the layout of therapeutic masses 550 across sheet 540 prior to wrapping. In the example shown in FIG. 18, sheet 540 comprises base panel 560 and cover panel 562.

Base panel 560 comprise a continuous sheet or panel of one or more biodegradable materials having cavities 566A, 566B, 566C, 566D and 566E (collectively referred to as cavities 566). Cavities 566 cooperate with cover panel 562 to form multiple compartments 574 encapsulating and containing therapeutic masses 550. In one implementation, cavities 566 are formed by removing material from a surface of panel 560. Such material removal may be performed by lasers, knives, chemical or physical etching, or by other material removal techniques. In yet other implementations, cavities 566 may be formed by selective addition of materials, such as through the use of masking, screening and the like. In other implementations, the pattern of cavities 566 in panel 560 may be formed through material shaping or deformation. For example, in some implementations, cavities 566 may be formed by embossing panel 560 while panel 560 is in an at least partially malleable or moldable state. In yet other implementations, cavities 566 may be formed by corrugating, bending or folding panel 560, wherein undulations in panel 560 form such cavities 566.

Cover panel 562 comprises a panel or sheet of one or more biodegradable materials joined to panel 560 to form chambers 570 so as to encapsulate or contain therapeutics within chambers 570. In one implementation, cover panel 562 is laminated to base panel 560 through welding, biodegradable adhesives and the like. Those portions of cover panel 562 overlying or extending across cavities 566 form caps for such cavities 566 to form chambers 570. Although each of the cavities 566 are illustrated as being closed or capped off with a single continuous cover panel 562, in other implementations, individual cavities 566 or subsets of such cavities 566 may be closed or capped off by separate individual cover panel 562.

Therapeutic masses 550 may comprise a same or different therapeutics of any of the type described above with respect to therapeutic masses 50. In one implementation, therapeutic masses 550 are applied to or deposited within their associated cavities 566 prior to joining of the one or more cover panels 562 to base panel 560. Such deposition of therapeutics may be carried out with a drop-on-demand inkjet printer, dispensing needles and the like. In other implementations, therapeutic masses 550 may be injected into cavities 566 of compartments 570 after such compartments 570 have been otherwise closed or sealed off by the one or more cover panels 562. For example, in some implementations, base panel 560 or cover panel 562 may be formed from a biodegradable material that function similar to a septum, allowing insertion of a needle or probe there through to allow therapeutics to be injected into a compartment 570, whereupon withdrawal of the needle or probe, the biodegradable material re-closes and re-seals.

FIGS. 18 and 18A illustrate various architectures and layouts by which the delivery of therapeutic masses 550 may be controlled using sheet 540 and therapeutic masses 550. As shown by FIG. 18A, the size and location of compartments 570 may be varied across sheet 540 to vary the amount of the therapeutic that is delivered as well as the timing at which such therapeutic is released (depending upon where the particular chamber 570 is formed on sheet 540 and how the sheet 540 is wrapped (wound or folded).

As shown by FIG. 18, the rate at which a therapeutic is released may be varied by adjusting or controlling the shape of the particular cavity 566. For example, an amount of therapeutics spread across a larger surface area of a shower, but wider and/or longer cavity 566 may be released or delivered at a faster rate as compared to the same amount of therapeutics contained in a deeper, but narrower (smaller opening) cavity 566. As noted above, in some implementations, a particular therapeutic mass 550, itself, may comprise therapeutic particles encapsulated within a biodegradable matrix that must dissolve for the therapeutic particles to be released and delivered.

As further shown by FIG. 18, the rate at which therapeutics are released or the timing at which such therapeutics are released may also be controlled by either varying the materials forming different caps of different compartments 570 or by varying the thickness of such different caps of different departments 570. For example, in one implementation, region 574 above cavity 566A may be formed from a biodegradable material that dissolves or otherwise degrades at a rate different than the biodegradable material or materials forming region 576 above cavity 566B. In one implementation, the thickness of cover panel 562 above cavity 566C (the cap of cavity 566C) is thinner as compared to the thickness of cover panel 562 above cavity 566D (the cap of cavity 566d). As a result, if such caps are otherwise the same and form from the same filler materials, the cap of cavity 566C may completely degrade before the cap of cavity 566D, releasing or delivering those therapeutics within cavity 566C before those therapeutics in cavity 566D.

In some implementations, the release of therapeutics may be controlled or varied amongst different compartments 570 by varying and controlling the depth of such compartments 570 with respect to the side of base panel 560 opposite to cover panel 562. For example, a cavity 566 may be sufficiently deep such that base panel 560 adjacent to a compartment 570 may degrade before or at the same time as the completion of degradation of the cap overlying the same compartment 570, allowing therapeutic masses 550 to be released from both sides of sheet 540. In the example illustrated in FIG. 18, cavity 566C is deeper than cavity 566B such that a bottom of compartment 574 from cavity 566C may become exposed (broken into) to release therapeutics from side 580 of sheet 540 prior to such an occurrence, if at all, through panel 560 opposite to cavity 566B. In some implementations, some cavities 566 may be configured to release therapeutics from both sides of sheet 540 while other of cavities 566 deliver therapeutics only through one side, either side 580 or side 582 of sheet 540.

In addition to controlling or varying the thickness of base panel 560 adjacent to cavities 556 to control the timing and rate at which therapeutic masses 550 are delivered, such delivery of therapeutic masses 550 may also be controlled by varying the biodegradable materials that form those regions or portions of base panel 560 adjacent to the different compartments 570. For example, portions of base panel 560 adjacent to cavity 566A may be selected chosen so as to biodegrade at a faster rate as compared to the bottom ratable material or materials forming those portions or regions of base panel 560 adjacent to cavity 566B. In some implementations, the materials chosen for base panel 560 (or cover panel 562) may be chosen to biodegrade at different rates due to the different therapeutic masses 550 or matrix material of such therapeutics contained within a cavity 566. For example, even though the material or materials of panel 560 and panel 562 may be the same adjacent to cavities 566A and 566B, such cavities 566A and 566B may contain different therapeutics are different therapeutic solvents or matrices that react differently with the material or materials forming panel 560 are forming panel 562. As a result, the particular material or material chosen for either of panel 560 or panel 562 in conjunction with the different characteristics of the therapeutic mass 550 or its surrounding matrix a result in a different time release of the different therapeutics.

Sheet 540 may be utilized to form body 22 of therapeutic delivery device 20. As described above, sheet 540 may be wrapped, such as being spirally wound as in FIG. 2 or folded as in FIG. 3 prior to being surrounded by outer shell 30. Sheet 540 may alternatively be severed or cut into individual smaller sheets and then stacked as in FIG. 15. In some implementations, multiple sheets 540 may be formed separately (not cut from a single sheet) and then stacked prior to being surrounded by outer shell 30.

In some implementations, sheet 540 (with therapeutic masses 550) may be implanted as a sheet (without being wound, folded or otherwise wrapped). In some implementations, outer shell 30 or core material 60 may be omitted.

For example, in each of the examples shown in FIGS. 2, 12 and 15, outer shell 30 and core material 60 may be omitted. In such implementations, body 22 may merely comprise the wrapped (wound or folded) or stacked arrangement of one or more sheets 40, 240, 340 or 540.

FIG. 19 schematically illustrates implantable device 620, another implementation of implantable device 20. Implantable device 620 similar to implantable device 20 except that implantable device 620 has a body 622 comprising multiple chambers 630A, 630B, 630C, 630D, 630E and 630F (collectively referred to as chambers 630). In addition to having an outer shell 30 and core material 60, body 622 includes intermediate biodegradable walls 632 that separate and form such chambers 630. Each of such chambers contains different therapeutics or different combinations of therapeutics in one implementation, each of such chambers 630 may have a different biodegradable core material 60 or a different biodegradable material or materials forming the adjacent outer shell portion 32 barrier control the rate of therapeutic delivery amongst the chambers. In the example illustrated, each of chambers 630 includes a different type of therapeutic delivery system including multiple smaller or miniature therapeutic delivery systems.

In the example illustrated, chamber 630A encloses or contains therapeutic delivery system similar to those shown in FIG. 2 formed from sheet 240 or sheet 540. Chamber 630B encloses or contains multiple different therapeutic delivery systems similar to those shown in FIGS. 2, 12 and 15 formed from sheet 240 or sheet 540. Chamber 630C contains a single type of therapeutic delivery system similar to those shown in FIG. 12 and formed from sheet 240 or sheet 540. Chamber 630D contains and encloses therapeutic delivery systems similar to those described with respect to FIG. 6. Chamber 630E contains or encloses therapeutic delivery systems similar those found in FIG. 15 and formed from sheet 240 or sheet 540. Chamber 630F surrounds or contains therapeutic delivery systems similar to those found in FIGS. 2, 12 and 15 and formed from sheet 240 or sheet 540.

Because chambers 630 include different types of therapeutic delivery systems, the rate at which therapeutics are delivered from such different chambers may be varied and controlled. For example, one delivery system may deliver therapeutics at a different rate or with different sequencing as compared to another delivery system. The combinations of delivery systems may be customized to provide a precisely controlled timing for the delivery of one or more therapeutics. In some implementations, different chambers 630 may contain different therapeutics are differ materials serving different functions. For example, in one implementation, one of chambers may contain material to facilitate tracking of a location of therapeutic delivery device 620. Examples of such materials may include the radio opaque material or a sonogenic material. At the same time, another of the chambers may contain a therapeutic while a third chamber contains a prophylactic antibiotic to decrease risk of infection post-implementation of the therapeutic delivery device inside the human or animal body. Although such chambers are illustrated as being in series along a length of device 620, in other implementations, such chambers may be formed within other chambers, make stand side-by-side in a radial or circumferential layout, or may have other arrangements.

FIG. 20 is a sectional view of body 722, another example of body 22 of therapeutic delivery device 20. Body 722 is similar to each of bodies 22, 122, 322 and 422 in that it facilitates a controlled time delayed release of therapeutics into a person or animal. Body 722 comprises shell 30 and core material 60 (described above) and porous member 740. Porous member 740 comprises a three-dimensional mass of the biodegradable material having open cells or open pores 744. Such cells or pores 744 are open and that they are interconnected to one another, allowing liquid to be absorbed by force member 740 such that inner cells or pores 744 may receive and contain liquid pass along through the series of cells or pores 744 are connected to the inner selves or pores 744 and extending to the outer perimeter of member 740. The walls 747 of such cells or pores 744 support, carry or are coated with therapeutic masses 750. Walls 747 form a plurality of layers throughout member 740 with such layers extending between portions of therapeutic masses 750.

Therapeutic mass 750 is similar to therapeutic masses 50, 250, 450 and 550 described above. Therapeutic mass 750 can be used en bloc as an implant, or wrapped, folded, stacked, etc. As before in FIGS. 2, 12, 15, or used as building block as 50 etc. When the implant 20 having body 722 is placed within an animal or human patient, outer shell 50 and core material 60 degrade. Thereafter, body 740 may begin to degrade and breakdown. As body 740 breaks down in degrades, therapeutic masses 750 are exposed and released. Innermost therapeutic masses 750 are released at later times since such innermost therapeutics are not exposed until outer layers of body 740 (walls 744) have broken down or biodegraded.

To adjust the timing of which therapeutic masses 750 are subsequently released, the density of the cells or pores may be adjusted. A greater density of cells or pores may result in a slower release of therapeutic masses 750 as more intervening layers must degrade or breakdown to expose inner therapeutic masses 750. A single body 740 may include different regions of different densities to achieve different non-uniform release rates. In some implementations, the intensity or concentration of therapeutic masses 750 (within liquid 950 described below) deposited or loaded into such cells or along such cells may be increased or decreased depending upon the corresponding density of pores or cells to achieve a desired rate of therapeutic release.

In the example illustrated, body 740 comprises a foam or sponge open celled material. In the example illustrated, body 740 comprises a biodegradable polymeric material in the form of a foam or sponge. In other implementations, body 740 may be formed from other biodegradable materials or may have other configurations to facilitate the absorption and retention of the liquid. In other implementations, shell 30 and/or core material 60 may be omitted.

FIG. 21 is a sectional view of body 822, another example of body 22 of therapeutic therapeutic delivery device 20. Body 822 is similar to each of bodies 22, 122, 322, 422 and 722 in that it facilitates a controlled time delayed release of therapeutics into a person or animal. Body 822 comprises porous member 840. Although illustrated as omitting shell 30 and core material 60, in other implementations, body 822 may additionally include shell 30 and/or core material 60. Porous member 840 comprises a three-dimensional mass of the biodegradable material having open cells or open pores 844. Such cells or pores 844 are open and are interconnected to one another, allowing liquid to be absorbed by member 840 such that inner cells or pores 844 may receive and contain liquid passed along and through the series of cells or pores 844 that are connected to the inner cells or pores 844 and which extend to the outer perimeter of member 840. The walls 847 of such cells or pores 844 support, carry or are coated with therapeutic masses 750. Walls 847 form a plurality of layers throughout member 740 with such layers extending between portions of therapeutic masses 750. Body 822 can be used in the form of a block as an implant, or may be wrapped, folded or stacked as before in FIGS. 2, 12 and 15.

Therapeutic masses 750 are similar to therapeutic mass 50, 250, 450 and 550 described above. When the implant 20 having body 822 is placed within an animal or human patient, body 840 begin to degrade in breakdown. As body 840 breaks down and degrades, therapeutic masses 750 are exposed and released. Innermost therapeutic masses 750 are released at later times since such innermost therapeutics are not exposed until outer layers of porous member 840 (walls 844) have broken down or biodegraded. In the example illustrated, body 840 comprises a three-dimensional reticulated structure, such as a three-dimensional textile, matrix or grid of biodegradable material having interconnected cells or pores into which liquid may be wicked.

In one implementation, porous member 840 may be woven. In another implementation, porous member 840 may be formed by sintering or by pressing a powder in a die. In yet other implementations, porous member 840 may be formed in other fashions.

FIGS. 22 and 23 schematically illustrate one example method of loading a porous member 940 (which may constitute a porous member such as porous member 740 or porous member 840) with therapeutic masses 750. As shown by FIG. 22, porous member 940 is dipped or submersed in a volume of liquid 950 containing either dissolved or suspended therapeutic particles 750. During such submersion, a vacuum from vacuum source 960 is applied to the container 962 containing liquid 950. The applied vacuum causes trapping gas or air within porous member 943 sucker drawn out of porous member 940 as indicated by arrow 965. As indicated by arrow 967, liquid 950 and therapeutic particles 750 are drawn into porous member 940 replacing the evacuated gas. The vacuum applied by source 960 creates a force so as to draw liquid 950 and particles 750 into porous member 940.

As illustrated in FIG. 23, the saturated or soaked porous member 940 is subsequently placed in a heating chamber 970 in which heat is applied to porous member 940 by heat source 972 to dehydrate porous member 940, evaporating the liquid (water or solvent) absorbed into porous member 940. In the example illustrated, vacuum source 974 additionally applies a vacuum to the interior of the heating chamber 970. As a result, the heat required to dehydrate porous member 940 is less, wherein the lower temperatures may result in less damage to therapeutic masses 750 or porous member 940. In other implementations, vacuum 974 may be omitted. As indicated by arrows 976, the liquid 950 saturating porous member 940 is removed from porous member 940, leaving the therapeutic particles 750 within and throughout porous member 940, coated upon the walls of such cells or pores. In embodiments where the implant has a core material 60 or shell 30, such additional structures may be subsequently added to porous the member 940. In other implementations, porous member 940 may be loaded with therapeutic masses 750 in other fashions. Again, the product of this process can be used individually as a core material, or rolled, folded, and wrapped as before.

Figure 26:
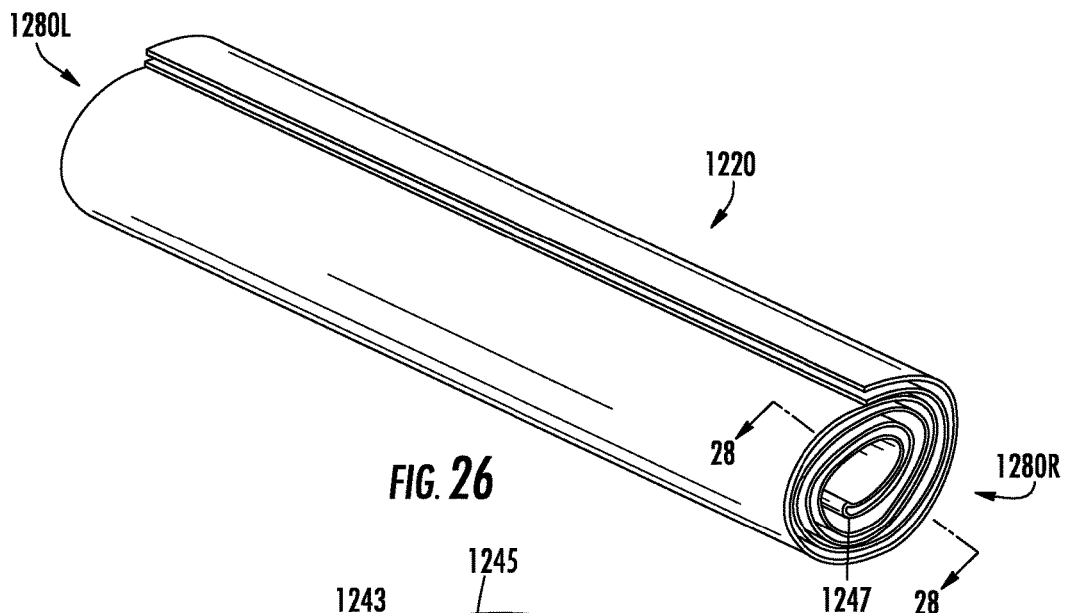
FIG. 26 is a perspective view of another example therapeutic delivery device.
Figure 27:
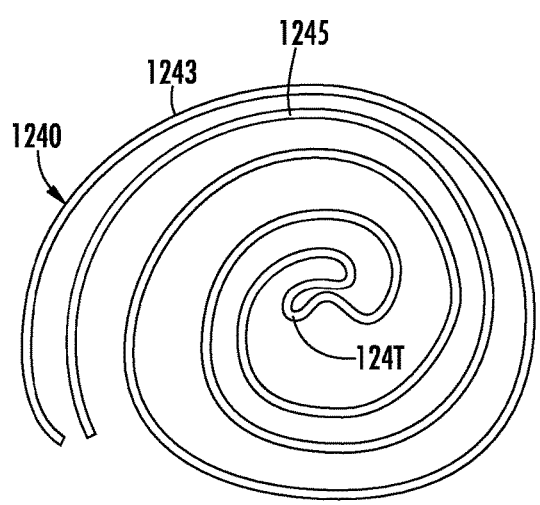
FIG. 27 is an end view of the therapeutic delivery device of FIG. 26.
Figure 28:
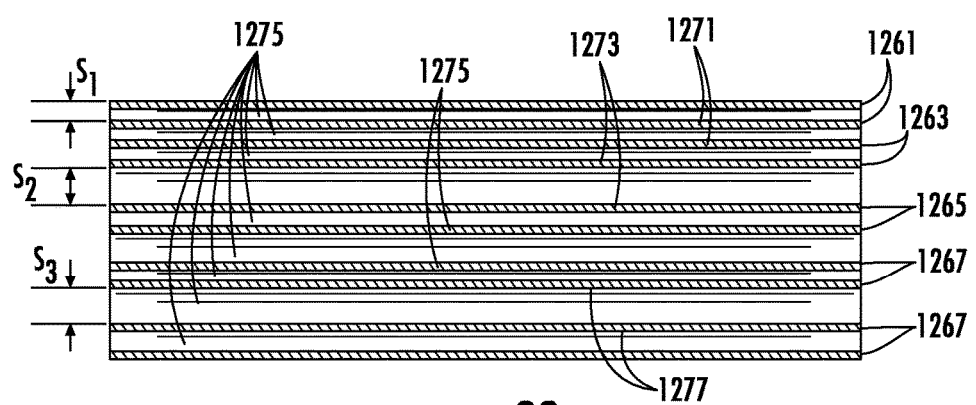
FIG. 28 is a sectional view of the therapeutic delivery device of FIG. 26 taken along line 28-28.

FIGS. 26-28 illustrate therapeutic delivery device 1220. In one implementation, therapeutic delivery device 1220 comprises an implant. In another implementation, therapeutic delivery device 1220 comprises an orally taken pill. Similar to the above described therapeutic delivery devices illustrated as implants, therapeutic delivery device 1220 delivers one or more therapeutics in a time released fashion.

As shown by FIG. 26-28, therapeutic delivery device 1220 is similar to therapeutic delivery devices 20, 1120 (shown as an implant) in FIG. 25 except that device 1220 comprises a layer or sheet of biodegradable material that is initially folded prior to being wrapped or wound. Device 1220 comprises sheet 1240 carrying or supporting therapeutic masses 50. In one implementation, sheet 1240 is similar to sheet 40 in that sheet 1240 comprises a membrane, film, panel or layer of biodegradable material therapeutic masses 50 are supported. In another implementation, sheet 1240 similar to sheet 1040 in that sheet 1240 comprises a laminate of multiple layers including a biodegradable supporting layer and a therapeutic layer. In another implementation, sheet 1240 is similar to sheet 1140 in that sheet 1240 comprises a layer of biodegradable material in which therapeutic masses 50 are embedded or otherwise incorporated therein. For example, such therapeutic masses may be homogeneously mixed into the material during the forming of sheet 1244 or may be doped or otherwise embedded into sheet 1240 at one or more selected locations. Therapeutic masses 50 are described above.

In the example illustrated, sheet 1240 comprises therapeutic masses which are each of homogenously dispersed throughout sheet 1240, selectively deposited upon sheet 1240 and selectively embedded into sheet 1240. In the example illustrated, sheet 1240 comprises a layer in which a baseline amount of therapeutics are homogeneously uniformly incorporated or dispersed. Additional therapeutic masses 50 are deposited incorporated into or embedded into sheet 1244 at selected locations. Yet additional therapeutic masses 50 are incorporated onto or deposited onto an outer surface of sheet 1244. As sheet 1244 degrades, the baseline amount of therapeutics forming a part of sheet 1244 are released. Those portions of sheet 1244 in which therapeutic masses 50 are embedded release an additional amount of therapeutics when being degraded. One mechanism for extended release from the layered structure is layer by layer degradation as discussed prior. Degradation and breaking down of a first portion of sheet 1244 may expose therapeutics located on the surface of another adjacent overlapping underlying winding of sheet 1244, allowing such surface deposited therapeutics to be delivered or released prior to the release of therapeutics incorporated into the portion of sheet 1244 that is covered or coated by the surface deposited therapeutics.

As further shown by FIGS. 26-28, sheet 1240 is folded so as to form overlapping portions 1243 and 1245 joined at spine, fold line or bend 1247. Bend 1247 is a junction between overlapping portions 1243, 1245. Bend 1247 facilitates the positioning of the opposing surfaces of portions 1243 and 1245 in close proximity to one another without or with minimal contact. The resilient nature of bend 1247 assists in supporting the opposing surfaces of portions 1243 and 1245 out of contact with one another with a more controlled spacing that is less dependent upon the tightness at which sheet 1240 is wrapped or wound.

As shown by FIG. 28, after being wound, overlapping portions 1243, 1245 form winding pairs 1261, 1263, 1265, 1267 and 1269. The winding of overlapping portions 1243, 1245 additionally forms winding pairs 1271, 1273, 1275 and 1277. In the example illustrated, the spacing between winding pairs 1261, 1263, 1265, 1267 and 1269 is substantially uniform amongst the pairs, dependent upon the tightness of the crease formed at bend 1247. The spacing S1 between winding pairs 1271, 1273, 1275 and 1277 is dependent upon the tightness at which the folded sheet 1240 is wound and any recoil of the winding pairs. In the example illustrated, the spacing S2 between winding pairs 1273 is larger than the spacing S3 between winding pairs 1277.

The spacing between such winding pairs determines the amount of gas or air captured between such winding pairs and also controls the extent to which such air is retained in place by surface tension or capillary action. The spacing between such winding pairs forms air or other gas containing pockets or layers 1275. In one implementation, the axial ends 1280L and 1280R of the wound sheet 1240 remain unoccluded or unsealed. In such an implementation, when bodily fluid's position along such axial ends, such bodily fluid is inhibited from flowing through the axial ends 1280 due to the air (or other gas) captured between the windings 1261-1275. Because the air or gas is held in place within device 1220 by capillary forces, for the bodily fluid to reach interior surfaces of device 1220 to begin degrading the biodegradable material of layer 1240 for the release of therapeutics, the bodily fluid, the bodily fluid must first absorb the air or gas. In other words, the air or gas must be dissolved by the bodily fluid for the bodily fluid to reach those interior portions of the wound layer 1240 and to begin degrading the biodegradable material of layer 1240. In one implementation, because the air or gas captured between windings 1261-1275 dissolves into bodily fluid at a rate much lower than the rate at which the biodegradable material degrades in such bodily fluid, the air serves as an enhanced barrier to facilitate time delays in the release or diffusion of therapeutics from the interior portions of device 1220. For example, of 100% air, 3% is carbon dioxide and live absorb instantaneously and contacting body fluid. 19% is oxygen which is used swiftly by the body. The remaining substantially 78% of air is nitrogen which is absorbed at a much slower rate. In one implementation, the absorption of nitrogen by body fluids occurs at a slower rate as compared to the rate at which the actual material sheet 1240 biodegrades while in contact with the body fluid. As a result, the air layers between the biodegradable winding layers serve as another variable to control the rate of therapeutic release, in addition to the layer by layer degradation mechanism discussed above.

Prior to being absorbed, the air (or remaining components of the air such as nitrogen) extend the release of the therapeutic in several manners. First, the gas layer or air pockets 1275 serve as an insulative layer, impeding or blocking ingress of the fluid towards the interior of delivery device 1220. As noted above, in one implementation, layer gas or air is not only thicker than the adjacent layer of sheet 1240 but also is absorbed by the body fluid at a rate slower than the rate at which layer sheet 1240 biodegrades when in contact with the body fluid. Second, the gas layer or air pockets 1275 additionally keep such therapeutics in a dry state. Many therapeutics de grade much slower at body temperature when dry as compared to when infiltrated with body fluids containing various chemicals and enzymes. The dry state of the therapeutics also inhibits outward diffusion of the therapeutics.

In one implementation, each gas layer 1235 has a thickness (corresponding to spacing S1, S2 and S3) of between 0.01 and 1 mm and nominally about 0.08 mm. In one implementation, each gas layer 1235 has a thickness of about 0.08 mm and is up to four times the thickness of the thickness of sheet 1240 which has a thickness of about 0.02 mm. With such dimensions, the capillary action of the body fluid is stronger than the tendency of the air within gas layer 1235 to form bubbles so as to escape from delivery device 1220. At the same time, the volume of air is sufficiently large to effectively facilitate regulation of the rate at which therapeutics are released/diffused.

In one implementation, sheet 1240 is formed from a material (such as the above-described PLGA 85/15 100 D and Doxorubicin mixture) and has a thickness (such as 0.02 mm) such that the windings formed by sheet 1240 are malleable, facilitating squeezing and bending of device 1220. As a result, device 1220 may conform to local tissue, bending and twisting upon body movement. At the same time, sheet 1240 is formed from material has a thickness so as to resist recoiling such that the windings maintain their shape and the spacings between such windings is consistent. In such an implementation, gas layers 1275 or compartments of gas between windings of sheet 1240 may shift. The shifting of the gas layers is dynamic, automatically adjusting in response to such movement or bending of delivery device 1220. Despite such shifting, capillary forces retain the gas layers between the windings.

Although therapeutic delivery device 1220 is illustrated as being formed from a single fold applied to sheet 1240 with the folded sheet 1240 having illustrated winding tightness, in other implementations, therapeutic delivery device 1220 alternatively comprises additional folds in different degrees of tightness. For example, in another implementation, sheet 1240 is folded multiple times, in an accordion like style having multiple fold lines or bends, prior to being wound. In another implementation, sheet 1240 is folded in a more compact or tighter arrangement. In another implementation, the folded sheet sheet 1240 is wound such that different winding pairs at different radial distances from the center of the sleeve of device 1220 have different spacings S. In yet another implementation, sheet 1240 is folded in a less compact or looser arrangement of windings.

In one implementation, sheet 1240 is formed at a temperature such that sheet 1240 is smooth, reducing a likelihood of adjacent windings sticking to one another during bending or twisting of delivery device 1220. In one implementation, sheet 1240 is formed while sheet 1240 is at a temperature less than a glass melting temperature of the membrane forming sheet 1240. For example, in one implementation, depending upon the molecular weight and ratio of glactide versus glycolide, sheet 1240 may have a glass melting temperature of between 30° C. and 60° C. By forming sheet 1240 while at attempt or less than the glass melting temperature, sheet 1240 is smoother, less likely to have its winding stick to one another when wrapped spirally to form the therapeutic delivery device. When delivery device 1220 is compressed when implanted, there is a greater chance that adequate air volume will be maintained and that the extent of recoil will be reduced so as to maintain protection of inner layers against premature release of therapeutics.

In one implementation, sheet 1240 is further formed while at a temperature above the ductile-brittle transition temperature of the material of the membrane forming sheet 1240. As a result, the material of sheet 1240 is less likely to break or shatter, but rather will bend or deform. By forming sheet 1240 at a temperature above the ductile-brittle transition temperature, malleability of the material is achieved such that sheet 1240 may be rolled or spirally wound. For the above-described example material PLGA 85/15 100 D and Doxarubicin mixture, the ductile-brittle transition temperature is approximately below −20° C. In one implementation, sheet 1240 is formed while at a temperature both above the ductile-brittle transition temperature of the material forming sheet 1240 and below the glass melting temperature of the material forming sheet 1240. In one implementation, sheet 1240 is formed while sheet 1240 is at a temperature of between −20° C. and 15° C., a temperature range that falls between the glass melting temperature and the ductile-brittle transition temperature of many biodegradable materials that may be used for sheet 1240.

Figure 29:
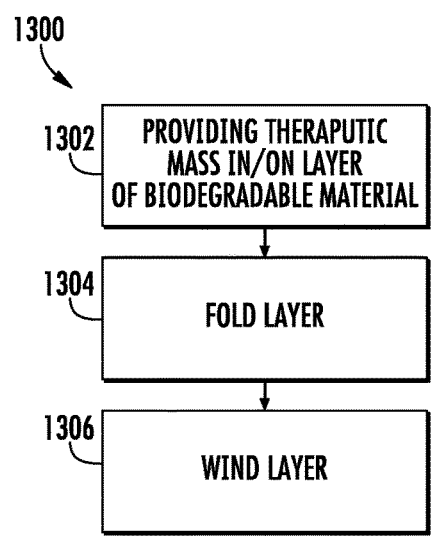
FIG. 29 is a flow diagram of an example method for forming the therapeutic delivery device of FIG. 26.
Figure 30:
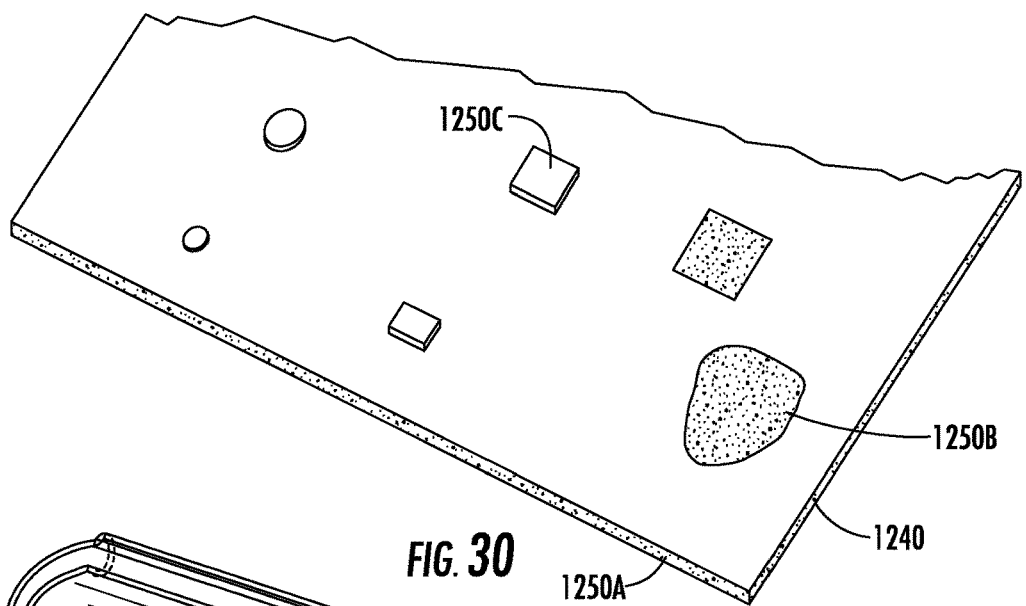
FIG. 30 is a fragmentary perspective view of a sheet and therapeutics prior to being folded or wound.
Figure 31:
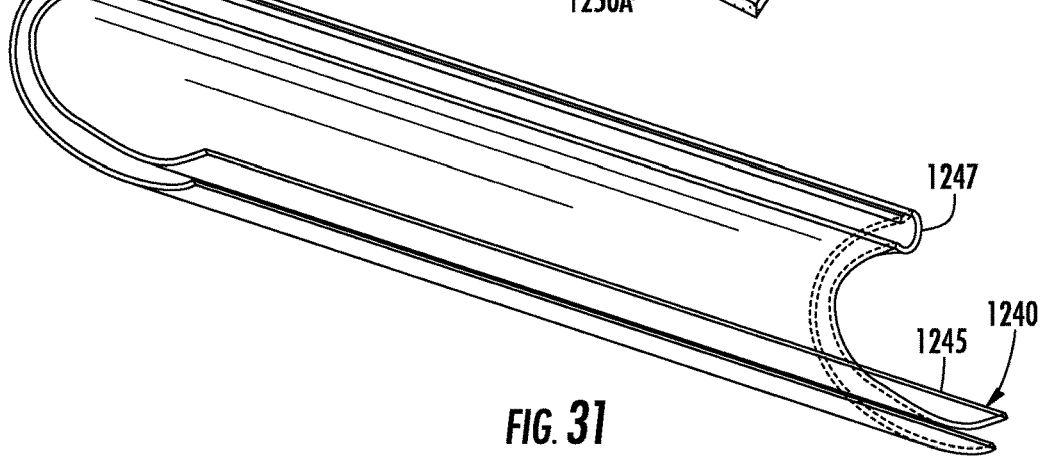
FIG. 31 is a perspective view of the sheet of FIG. 30 after being folded and prior to being wound as shown in FIG. 26.

In addition to or as an alternative to forming sheet 1240 while sheet 1240 is at a temperature below the glass melting temperature, sheet 1240 may be smoothed through grinding or polishing operations carried out upon one or both surfaces of sheet 1240. In one implementation, those opposite faces or surfaces of sheet 1240, surfaces that may contact one another after sheet 1240 have been wound and upon bending or compression of therapeutic delivery device 1220, have a coefficient of friction of between 0.1 and 0.5 (the coefficient of friction being a measure of sheet 1240 on sheet 1240). In one implementation, each layer are winding of therapeutic delivery device 1220 maintains its diameter, recoiling no more than 20% after rolling pressure is released. Therapeutic delivery device 1220 is also configured to recall back to its original volume after being compressed by up to 30% of his original volume FIGS. 29-31 illustrate an example method for forming a therapeutic delivery device 1220 shown in FIGS. 26-28. FIG. 29 is a flow diagram of an example method 1300 for forming therapeutic delivery device 1220. As indicated by block 1302, one or more therapeutic masses 1250 provided in on a layer are sheet of biodegradable material. FIG. 30 illustrates sheet 1240 prior to folding or winding. As shown by FIG. 30, sheet 1240 includes therapeutic masses 1250A, 1250B and 1250C (collectively referred to as therapeutic masses 1250 or therapeutics 1250). Therapeutic masses 1250A comprise therapeutics that are homogenously or uniformly dispersed throughout material of sheet 1240. In one implementation, the amount of therapeutics 1250A dispersed throughout sheet 1240 is a baseline are minimal amount for release.

Therapeutic masses 1250B comprise therapeutics that are embedded or deposited at a selected regions are locations of sheet 1240. Those regions of sheet 1240 which include therapeutic masses 1250B have a greater density of therapeutics as compared to other regions of sheet 1240 which do not include therapeutics 1250B or 1250C. The regions of sheet 1240 at which therapeutics 1250B are embedded is controlled so as to control the eventual timing at which the increased amount for density of therapeutics is released. For example, therapeutics to be released at an earlier time will be deposited in regions of sheet 1240 which will be located closer to the exterior of device 1220.

Therapeutic masses 1250C comprise therapeutics that are coated or deposited upon an outer surface of sheet 1240. Because such therapeutic masses 1250C project above the underlying surface, such therapeutic masses 1250C a greater surface area surrounded by the bodily fluid when exposed (as compared to therapeutics 1250A and 1250B which are at least partially surrounded by the adjacent biodegradable material of sheet 1240). As a result, therapeutic masses 1250C are diffused and are released at a greater rate.

By controlling the manner in which therapeutics are carried by sheet 1240, whether it be by being they fused uniformly throughout sheet 1240, embedded within sheet 1242 form intense regions of therapeutics or deposited upon the service sheet 1240, the rate which said therapeutics are diffused and released is controlled. As further shown by FIG. 30, the rate at which the therapeutics are provided is further controlled by controlling not only the location of such therapeutics on sheet 1240, but also the size, shape and thickness/density of such therapeutics at the particular regions. Although sheet 1240 is illustrated as including a combination of each of therapeutics 1250A, 1250B and 1250C, in other implementations, the therapeutics delivered by sheet 1240 may alternatively consist of therapeutics in fewer forms. For example, sheet 1240 alternatively comprises therapeutics only in the form of therapeutics 1250A, therapeutics only in the form of therapeutics 1250B, therapeutics only in the form of therapeutics 1250C or a combination of two of the described forms of therapeutics. Although therapeutics 1250C are illustrated as being coated upon one face of sheet 1240, the face that forms the inside faces of the folded sheet 1240, in another implementation, therapeutics 1250C or alternatively formed upon one face of sheet 1240, the face that forms the outside faces of the folded sheet 1240. In yet another implementation, therapeutics 1250C are coated upon both faces of sheet 1240 prior to folding.

As indicated by block 1304 FIG. 29, once therapeutics 1250A, 1250B and 1250C have been incorporated into or on sheet 1240, sheet 1240 is folded. FIG. 31 illustrates the folding of sheet 1240 along a single fold line or bend 1247. As noted above, in other implementations, sheet 1240 may be folded along additional fold lines or bends to form more than two overlapping portions. As discussed above, bend 1247 assists and controlling and regulating the spacing between the subsequent formed windings formed by overlapping portions 1243 and 1245 of sheet 1240.

As indicated by block 1306, once folded, sheet 1240 is wrapped or wound. FIG. 26 illustrates folded sheet 1240 after it has been wound. Once wound, the ends of the folded sheet are secured in place by biodegradable adhesive, stitching or other securement methods. One implementation, the wound folded sheet 1240 and the provided therapeutics 1250 are directly implanted or directly swallowed. In another implementation, the wound folded sheet and the provided therapeutics 1250 are surrounded by a shell 30 or are surrounded by a filler material 60 and an outermost shell 30.

Figure 32:
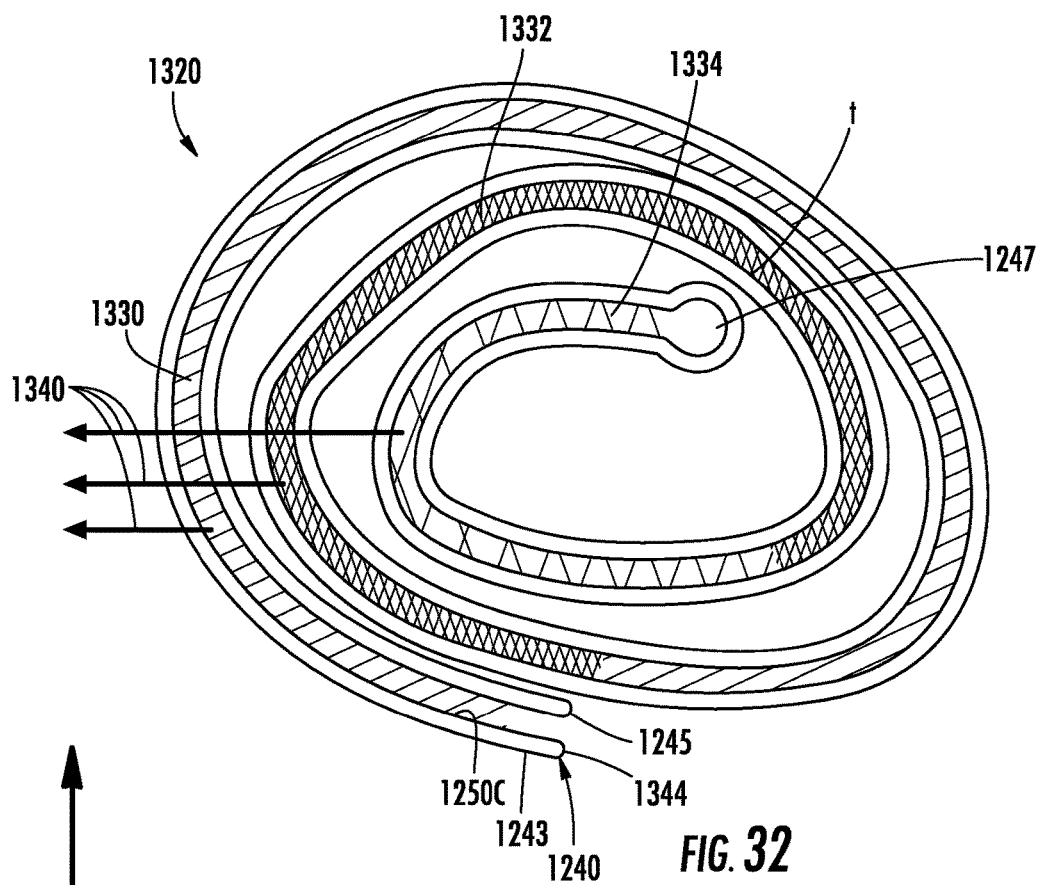
FIG. 32 is a sectional view of another example therapeutic delivery device.

FIG. 32 is a cross-sectional view of therapeutic delivery device 1320. Therapeutic delivery device 1320 is similar to therapeutic delivery device 1220 except that therapeutic delivery device 1320 omits therapeutic masses 1250A and 1250B. Therapeutic delivery device 1320 comprises sheet 1240 carrying therapeutic masses 1250C deposited on one face of sheet 1240, the face that forms the two mutually facing surfaces of overlapping portions 1243, 1245. As shown by FIG. 32, therapeutic delivery device 1320 comprises three different zones 1330, 1332 and 1333, which release therapeutics 1250C or from which therapeutics 1250C diffuse at different times. Therapeutics 1250C are released from zone 1330 as they are contained in the outermost windings of device 1320. Therapeutics 1250C are released from zone 1332 as they are contained in the intermediate region of windings. Therapeutics 1250C are released from zone 1334 as they are contained in innermost windings of device 1320.

Upon delivery device 1320 being implanted inside the anatomy of a person or animal, body fluid infiltration begins. Therapeutic fusion also is initiated. Initially, the body fluid infiltrates or penetrates only the first interlayer space, wherein the therapeutic in such contacted area areas diffuse out. This process continues on for the next inter-winding space until the center is reached. Upon the interior portion of the device 1320 carrying therapeutics being contacted by body fluid infiltrates, a concentration difference is established such that therapeutic concentration we higher than the bottom fluid outside of the device 1320. To establish osmatic pressure, the contacted therapeutics move in an opposite direction of the body fluid infiltrates, diffusing outwardly. In one implementation, therapeutics diffuse through the windings of layer 1240 (referred to as cross layer diffusion) as indicated by arrows 1340. The rate at which therapeutics diffuse across and out of device 1320 is inversely related to the number of windings or wound layers.

The layered structure serves as yet another mechanism for extended release, in addition to the two mechanism discussed before, the layer by layer degradation and the air layer slow down of tissue fluid ingression inside the inner layer of the device. The deeper therapeutic is placed within the device, the more layers of material, or the more windings, the therapeutic must diffuse across, extending the release in a precisely controlled manner for weeks or even months. However, this is assuming the outer layers remain intact for weeks and months inside the living body at about 37 degrees Celsius. Accordingly, the layer of material comprises one or more materials that withstand the body fluids' degration effect, such as hydrolysis, enzymatic or varieties of chemical breakdown (e.g., acidic, basic).

In one implementation, the layer of material comprises a membrane of PLGA85; 15 D100 wound at 0 celsius degree to form the windings of the device. The polymers in PLGA solidify at this temperature, wherein the membrane is rolled into the windings of the implantable device. The resulting therapeutic device has extended durability compared to the same device that is made and rolled at 25 Celsius degrees Celsius implanted in a mouse model. Because the therapeutic device is formed at a lower temperature, such as below 15 degrees Celsius, the windings of the device are more durable. This increased durability is likely due to polymerization of the biodegradable polymers being more densely packed and oriented in a more unified direction. In addition, the membrane or layer formed and wound at the lower temperature has properties that are closer to the desired malleability and smoothness for the implant device.

The three above described release mechanisms cooperate to delay or extend the release of the therapeutic. For PLGA based material, as the molecular weight of the starting polymers decrease, the ease at which the material degrades in the body increases. As a result, a therapeutic delivery device made windings of a PLGA based material having a low molecular weight may last for days inside body, and degradation will play a bigger part for any extended release. By way of contrast, a device made of higher molecular weight polymer will have weeks for degradation. By controlling the number of windings or the extent of layering the rate at which diffusion across multiple layered occurs is controlled. In some implementations, the extra air layers may prolong the release of the therapeutics for greater durations of time. For extended release beyond 1-3 weeks, the air layer mechanism plays an even larger role.

Diffusion of therapeutics may additionally occur may additionally occur through the opening 1344 between overlapping portions 1243, 1245 as well as through the axial ends 1280L, 1280R (shown in FIG. 26). Diffusion through the axial ends or through opening 1344 is relatively small relative to the cross layer diffusion due to proportional size. In some implementations, opening 1344 or the axial ends 1280L, 1280R are at least partially closed or sealed to control/diffusion of therapeutics from device 1320 through such openings.

Figure 33:
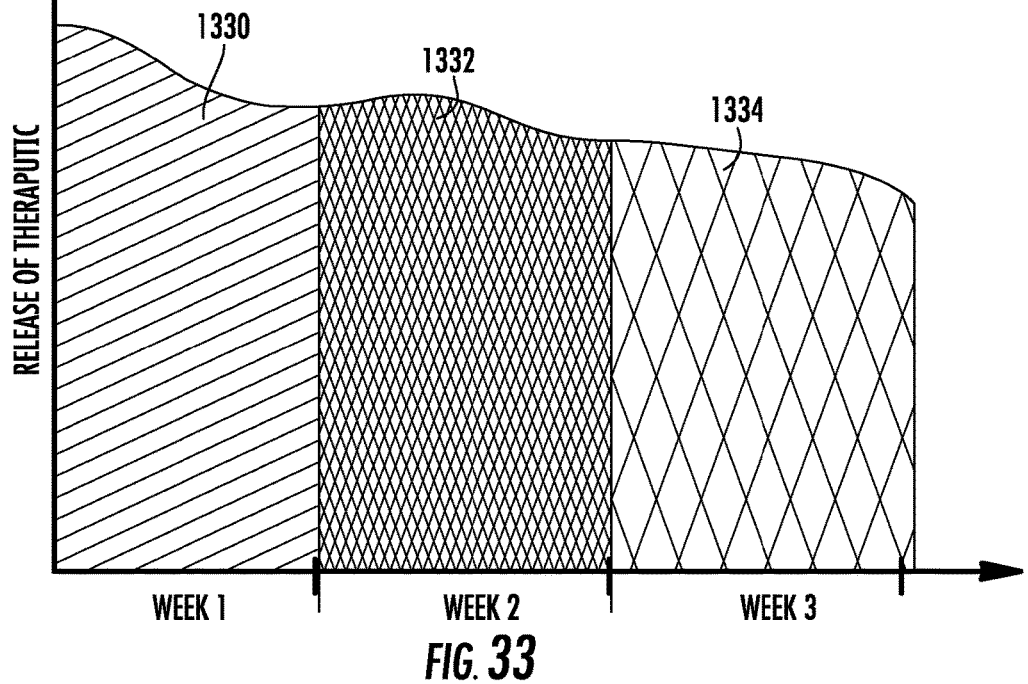
FIG. 33 is a graph illustrating timed release of therapeutics from the therapeutic delivery device of FIG. 32.

FIG. 33 is a graph illustrating the release of therapeutics 1250C from device 1320 over time. As shown by FIG. 33, therapeutic delivery device 1320 releases therapeutics over a three-week time span utilizing all of the 3 extended release mechanisms discussed above: the layer by layer degradation, the air layer slow down, and diffusion through multiple layers. Therapeutics from zone 1330 are released in week one. Therapeutics from zone 1332 are released in week two. Therapeutics from zone 1334 are released in week three. The release curve shown in FIG. 33 may be modified to release therapeutics at an increasing rate over time, at a decreasing rate over time are at a relatively level or flat rate over time. In contrast to systemically administered therapeutics, which may have trough to peak cycles, implementations of device 1320 are configured to avoid such concentration swings, similar to intramuscularly administered medicines. Concentrations of therapeutics delivered by device 20 are high enough to achieve therapeutic effect of the low enough to avoid local toxicity issues. As a result, device 1320 is well-suited for delivering therapeutics for vast application, for example pain control, cancer treatment, diabetic treatment and deliveries of insulin secreting cells.

Figure 34:
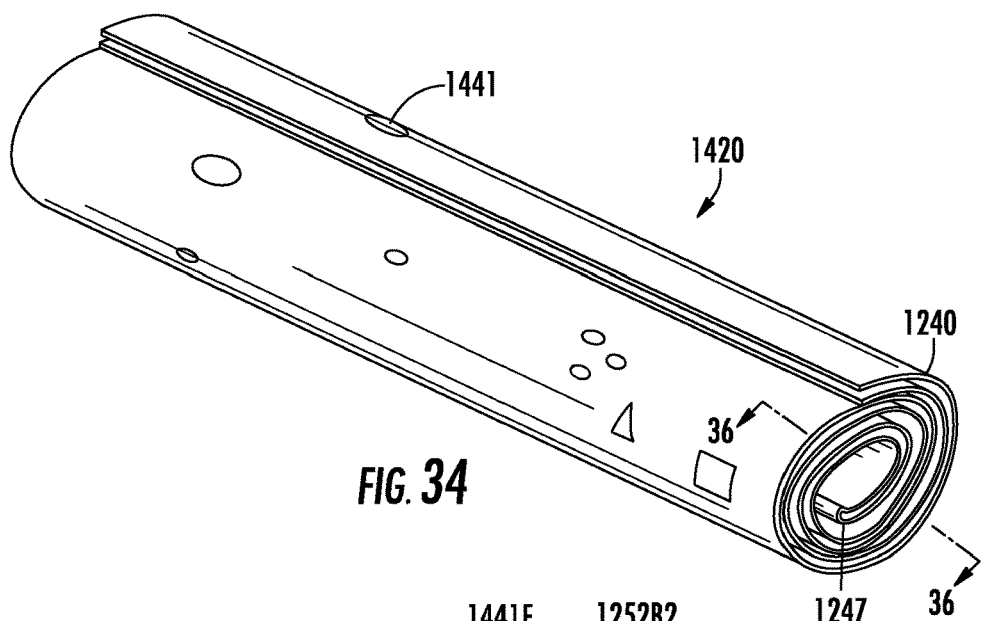
FIG. 34 is a perspective view of another example therapeutic delivery device.
Figure 35:
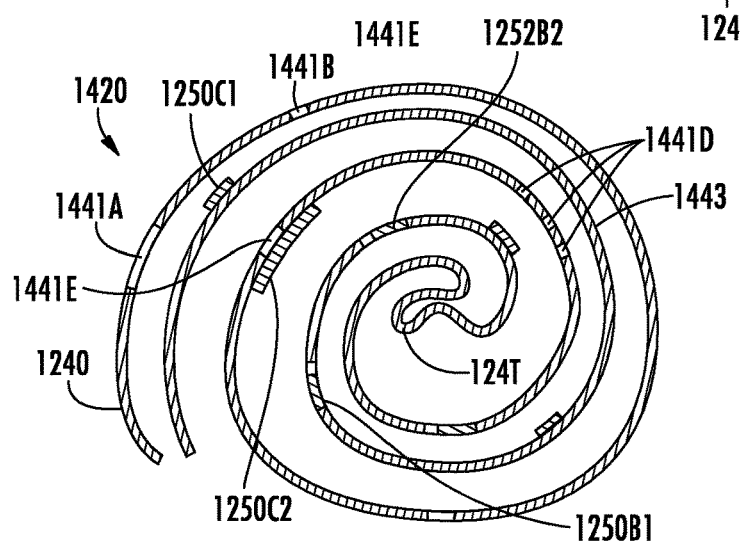
FIG. 35 is an end view of the therapeutic delivery device of FIG. 34.
Figure 36:
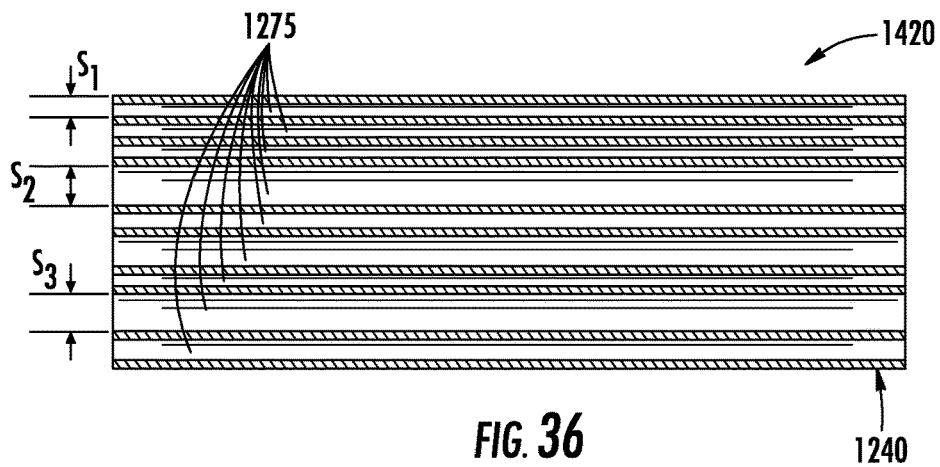
FIG. 36 is a sectional view of the therapeutic delivery device of FIG. 26 taken along line 28-28.

FIGS. 34-36 illustrate therapeutic delivery device 1420, another example implementation of therapeutic delivery device 1220. Therapeutic delivery device 1420 is similar to delivery device 1320 except that the delivery device 1420 additionally comprises perforations 1441. Those remaining components of delivery device 1420 which correspond to components of delivery device 1220 are numbered similarly.

Perforations 1441 comprise holes, apertures, slits or the like extending through sheet 1240. Perforations 1441 facilitate faster ingress of body fluid through portions of device 1422 further control the rate at which selected therapeutics of device 1420 are diffused or otherwise released. In the example shown in FIGS. 34-36, perforations 1441 vary in location, size and shape so as to vary diffusion characteristics of device 1420. For example, as shown by FIG. 35, perforations 1441 comprise perforations 1441A and 1441B. Perforations 1441A and 1441B both extend through the same winding of sheet 1240, but are circumferentially spaced from therapeutic mass 1250C1 by different distances. As a result, therapeutic 1250C1 may diffuse through perforation 1441A at a greater rate. In the example illustrated, perforation 1441A is also larger than perforation 1441B, further facilitating a greater diffusion rate through perforation 1441A.

In the example illustrated, perforations 1441 further comprise perforations 1441D. Perforations 1441D extend through an interior winding of sheet 1240 such that perforations 1441D are not immediately exposed to body fluid when placed within a person or animal, but are overlapped, covered and protected by an overlying imperforate portion 1443 of the next adjacent outer winding of sheet 1240. As shown by FIG. 35, perforations 1441D comprise a series of smaller perforations arranged close to one another. By varying the quantity or density of perforations 1441 at different regions of sheet 1240 or by varying the size, shape or location of perforations 1441, as with perforations 1441A and 1441B, diffusion of therapeutics from device 1420 is controlled.

Perforations 1441 further comprise example perforations 1441E and 1441F. Perforation 1441E extends through a winding of sheet 1240 directly opposite to or beneath/above and adjacent therapeutic mass 1250C2. As a result, opposite faces of therapeutic mass 1250C2 are concurrently exposed. Perforations 1441F extends through the winding if sheet 1240 adjacent to or alongside therapeutic masses 1250B1 and 1250B2 which are embedded in sheet 1240. Perforations 1441F expose edges are sides of masses 1250B1 and 1250B2 to enhance the rate of diffusion of such therapeutics. At the same time, perforations 1441F facilitate the ingress of body fluid in the diffusion of therapeutics across the particular winding in which the perforations 1441F are located.

Figure 37:
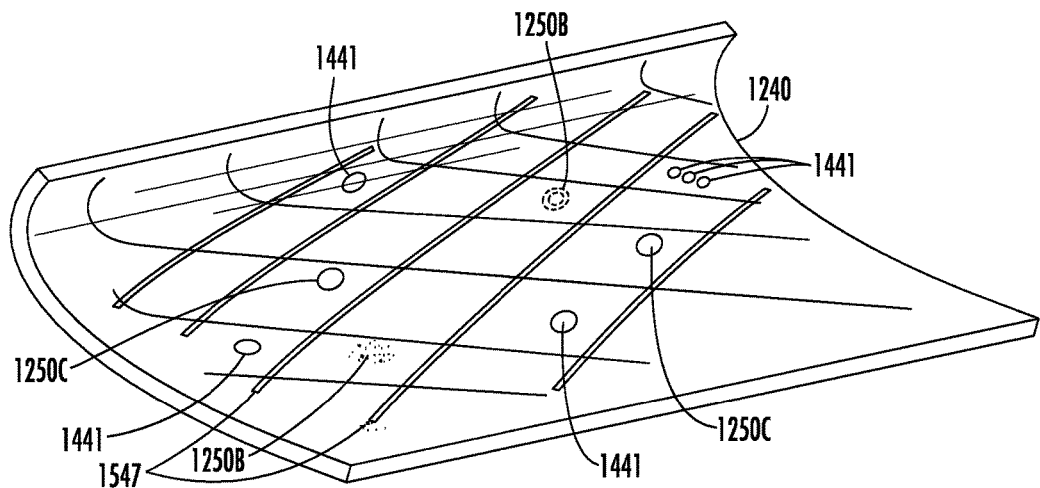
FIG. 37 is a perspective view of the sheet of FIG. 30 additionally comprising spacers and perforations.
Figure 38:
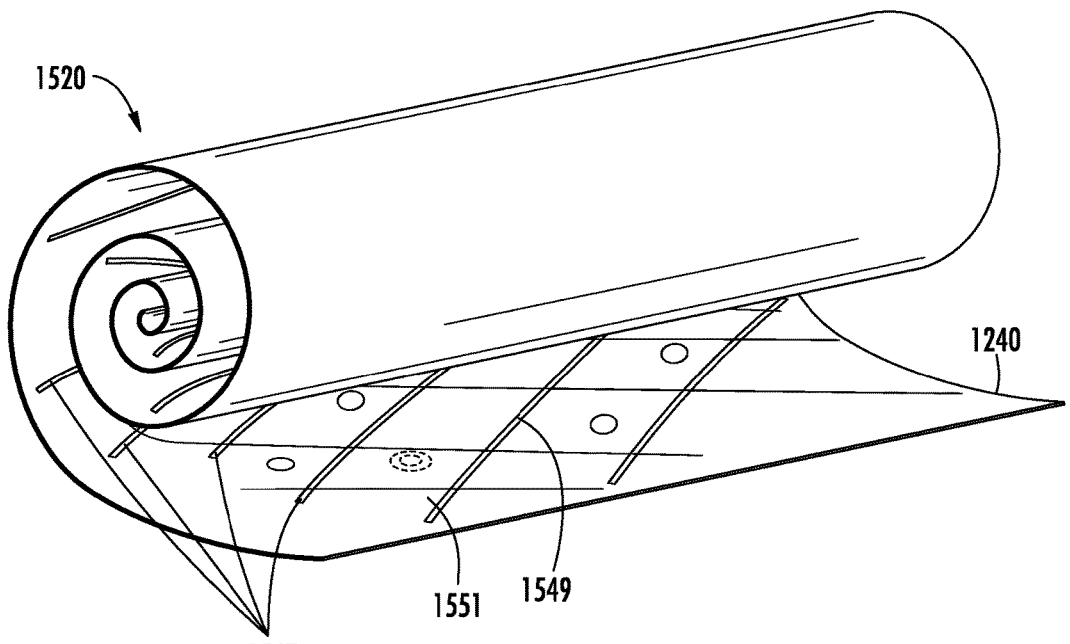
FIG. 38 is a perspective view of the sheet of FIG. 37 during winding.

FIGS. 37 and 38 illustrate the formation of therapeutic delivery device 1520. Therapeutic delivery device 1520 is similar to therapeutic delivery device 1220 and therapeutic delivery device 1420 except that therapeutic delivery device 1520 is not formed from a sheet that is folded prior to wrapping or winding. Instead of utilizing a bend or fold line to facilitate control over spacing between adjacent windings of the sheet, therapeutic delivery device 1520 utilizes one or more spacers 1547 which control spacing between adjacent windings. Those components are elements of therapeutic delivery device 1520 which correspond to elements or components of therapeutic delivery device 1220 or therapeutic delivery device 1420 are numbered similarly.

In the example shown in FIGS. 37 and 38, spacers 1547 comprise grids extending along at least one face of sheet 1240. In particular, spacers 1547 comprise a series of raised projection lines extending along at least one major face of sheet 1240 so as to form recesses 1549 between such raised projection lines. Recesses 1549 provide volumes which contain a gas, such as air, when sheet 1240 is wound or wrapped. As discussed above, the captured gas or air between the windings of sheet 1240 facilitates control over the rate at which therapeutics are diffused or otherwise released.

In one implementation, the grids serving as spacers 1547 are bonded, adhered, stitched, welded or otherwise secured to face 1551 of sheet 1240. In one implementation, spacers 1547 are formed upon surface 1551. In another implementation, the grid serving a spacers 1547 are integrally formed as a single unitary body with sheet 1240. For example, in one implementation, sheet 1240 is molded or embossed to form the grids serving as spacers 1547. In another implementation, portions of sheet 1240 are removed to form recesses 1549 between spacers 1547. In one implementation, both major opposing faces of sheet 1240 are provided with grids serving as spacers 1547. Although sheet 1240 in FIG. 37 is illustrated as including perforations 1441, described above, in other implementations, sheet 1240 may omit such perforations. In one implementation, sheet 1240 including spacers 1547 is folded prior to being wound.

As shown by FIGS. 37 and 38, sheet 1240 with spacers 1547 is rolled or wound to form delivery device 1520. During such winding, spacers 1547 contact and bear against the opposite face of sheet 1240 (whether the opposite surface be flat or whether the opposite surface contain additional spacers 1547) to capture air or gas between the windings. As a result, the captured gas, such as air, assists in regulating the rate at which therapeutics 1250A, 1250B or 1250C, described above, are diffused or otherwise released from between the windings.

Figure 39:
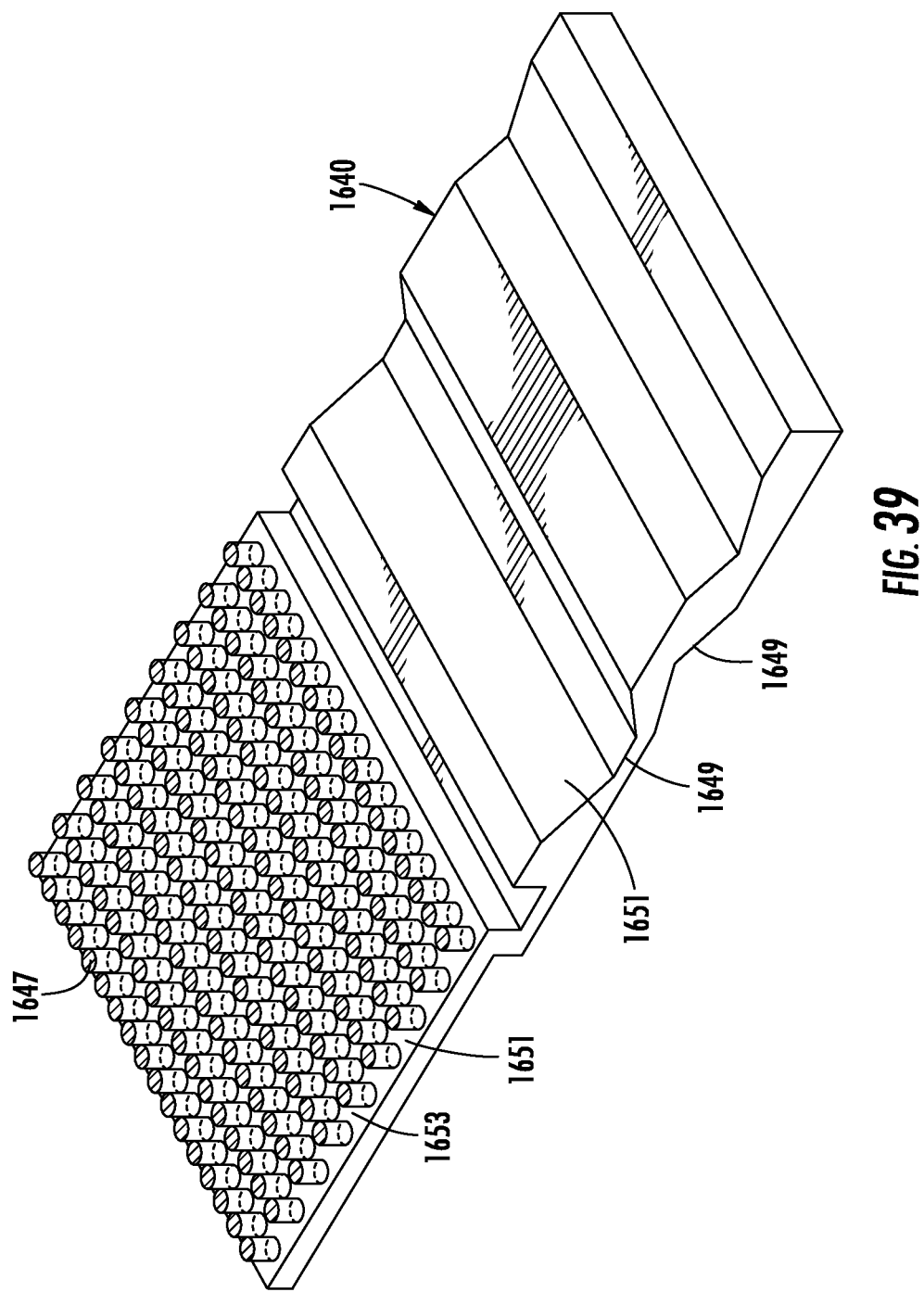
FIG. 39 is a perspective view of another example implementation of the sheet of FIG. 30.

FIG. 39 illustrates sheet 1640, an example implementation of sheet 1240. As with sheet 1240, sheet 1640 is provided with therapeutic masses, such as therapeutic masses 1250A, 1250B and 1250C described above. As with sheet 1240, sheet 1260 utilizes captured gas or air between the windings to regulate the rate at which such therapeutic masses are released or diffused to the surrounding blood flow or surrounding anatomy.

Sheet 1640 comprises posts 1647, and concave depressions 1649. Posts 1647 comprise an array of columns, bristles or other projections extending from face 1651, forming gas or air containing gaps or recesses 1653 between and amongst posts 1647. When sheet 1640 is wound to form a therapeutic delivery device, the tops of posts 1647 contact or abut the opposing portions of sheet 1640 of an adjacent winding. Although sheet 1240 is illustrated as having posts 1647 with illustrated sizes, shapes and an illustrated density or spacing, in other implementations, posts 1647 may be provided on sheet 1640 with other sizes, shapes, densities or spacings depending upon the desired rate at which therapeutics are to be delivered and diffuse from the wound sheet 1640. Although sheet 1640 is illustrated as having posts 1647 on a single side of sheet 1640, in other implementations, sheet 1640 may include posts 1647 on both opposite faces.

Concave depressions 1649 comprise portions of sheet 1240 having reduced thicknesses thus to form such concave recesses are depressions. In the example illustrated, concave depression 1649 comprise elongated grooves or channels formed along surface 1651 of sheet 1640. When sheet 1640 is wound, portions of sheet 1640 having higher elevations contact or abut surfaces of the adjacent winding while depression 1649 retain or capture air to regulate the subsequent diffusion or release of therapeutics. As shown by FIG. 39, in one implementation, both opposite sides of sheet 1640 comprise concave depression 1649. In other implementations, such concave depression 1649 are provided on a single side of sheet 1640, wherein the other side remains flat.

Figure 40:
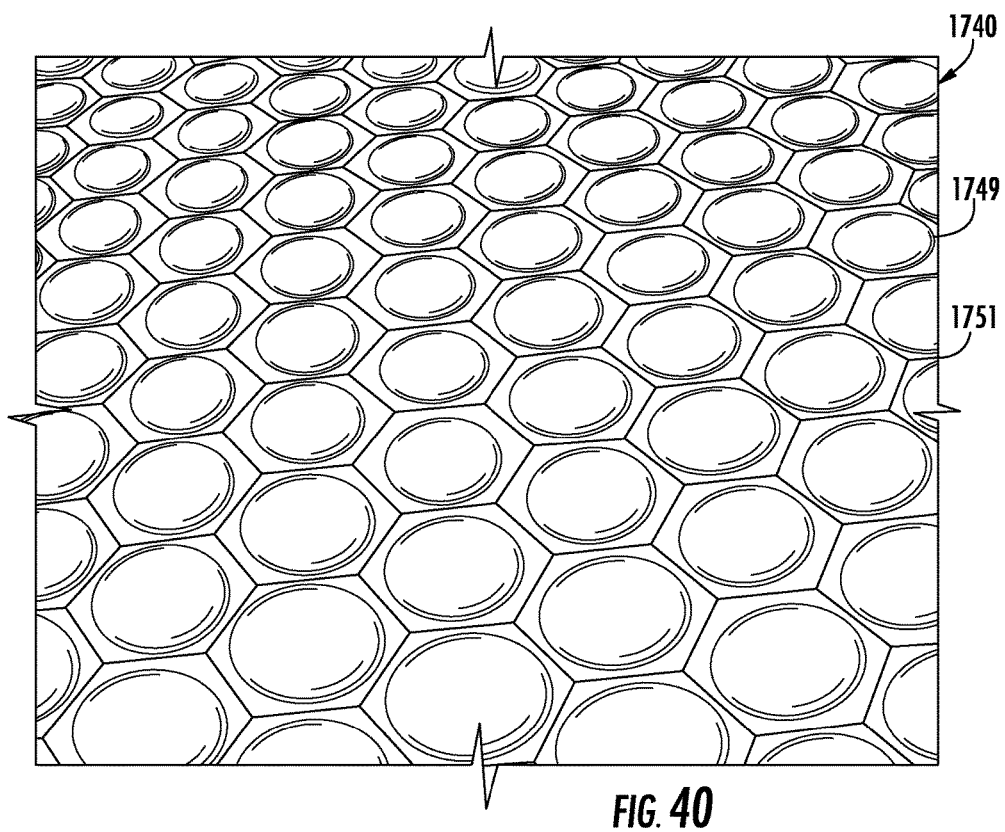
FIG. 40 is a fragmentary perspective view of another example implementation of the sheet of FIG. 30.

FIG. 40 illustrates sheet 1740, yet another example of sheet 1240. Sheet 1740 comprises concave depressions 1749. Unlike concave depression 1649 which are in the forms of grooves or channels, concave depressions 1749 comprise pockets, pits, craters or other depressions extending into surface 1751 and isolated from adjacent depression 1749. In the example illustrated, concave depressions 1749 comprise spherical craters ranging a cell-like pattern across surface 1751. When sheet 1740 is wound, the higher elevation portions of surface 1751 surrounding such depressions 1749 contact or abut the surface of the adjacent opposing winding such that depression 1749 form substantially close off or sealed pockets or capsules containing gas or air that regulates the release or diffusion of therapeutics (in the form of therapeutic masses 1250A, 1250B and/or 1250C) provided by sheet 1740. In other implementations, depression 1749 may have other sizes, shapes and/or densities along surface 1751.

Figure 41:
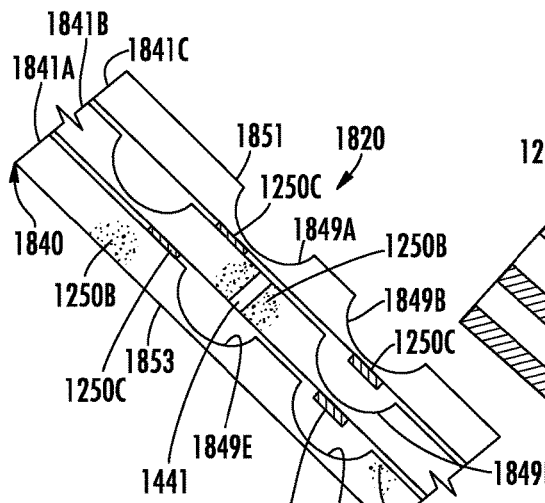
FIG. 41 is a fragmentary sectional view of a portion of another example therapeutic delivery device.

FIG. 41 is a sectional view illustrating a portion of therapeutic delivery device 1820, an example implementation of therapeutic delivery device 1220 described above. Therapeutic delivery device 1820 comprises one or more sheets 1840 wound to form a plurality of windings. FIG. 41 illustrates three of such windings 1841A, 1841B, 1841C (collectively referred to as windings 1841). In the example illustrated, such windings 1841 are formed by the winding of a single sheet 1840. In other implementations, such windings 1841 may be formed by a plurality of such sheets 1840.

As shown by FIG. 41, sheet 1840 comprises a plurality of concave depressions 1849A, 1849B, 1849C, 1849D, 1849E and 1849F (collectively referred to as concave depressions 1849) on a first face 1851 and further comprises a flat smooth opposite face 1853. In one implementation, concave depressions 1849 are similar to concave depression 1749 described above. In still another implementation, concave depressions 1849 are similar to concave depression 1649, in the form of grooves or channels. Sheet 1840 is wound to form windings 1841. Concave depressions 1849 are sealed off or closed off by the overlying portion of surface 1853 of the adjacent winding to capture or trap air within such concave depressions 1849, wherein such trapper captured air system in regulating the release or diffusion of therapeutic masses 1250. For example, concave depression 1849 of winding 1841B is illustrated as being close off are sealed by surface 1853 of winding 1841C.

In the example illustrated, the relative locations of depressions 1849 of adjacent windings may be controlled or varied to further regulate the rate at which therapeutic masses are released or diffused from device 1820. For example, concave depressions 1849A, 1849 C and 1849C are all circumferentially offset are staggered relative to one another. As a result, biodegradation of windings 1841 and diffusion through such portions of windings 1841 below depressions 1849A, 1849C and 1849E is slowed due to the full thickness of sheet 1840 below such depressions. In contrast, depressions 1849B, 1849D and 1849F are circumferentially aligned with one another. As a result, biodegradation of windings 1841 and diffusion through such portions of windings 1841 below depressions 1849B, 1849D and 1849F is faster due to the reduced thickness of sheet 1840 below such depressions. In the example illustrated, therapeutics located below winding 1841A in regions circumferential aligned with depressions 1849B, 1849D and 1849F moving more quickly released or diffused as compared to therapeutics located below winding 1841A in region circumferentially aligned with depression 1849E.

In the example illustrated, sheet 1840 is illustrated as including therapeutics in the form of therapeutic masses 1250B and 1250C (described above). Sheet 1840 is further illustrated as comprising perforations 1441 (described above). In other implementations, sheet 1840 includes therapeutics in the form of therapeutic masses 1250A, 1250B, 1250C or various combinations of masses 1250A-1250C. In other implementations, sheet 1840 may omit perforations 1441.

Figure 42:
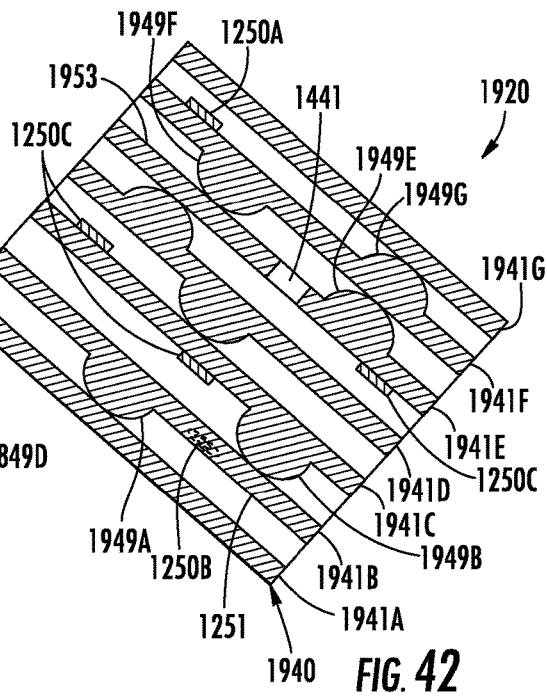
FIG. 42 is a fragmentary sectional view of a portion of another example therapeutic delivery device.

FIG. 42 is a sectional view illustrating a portion of therapeutic delivery device 1920, another implementation of therapeutic delivery device 1220. Therapeutic delivery device 1920 comprises one or more sheets 1940 wound to form a plurality of windings. FIG. 42 illustrates seven of such windings 1941A, 1941B, 1941C, 1941D, 1941E, 1941F and 1941G (collectively referred to as windings 1941). In the example illustrated, such windings 1841 are formed by the winding of a single sheet 1940. In other implementations, such windings 1941 may be formed by a plurality of such sheets 1940.

As shown by FIG. 42, sheet 1940 comprises a plurality of convex bumps 1949A, 1949B, 1949C, 1949D, 1949E, 1949F in 1940 9G (collectively referred to as convex bumps 1949). Convex bumps 1949 rise above or project from the respective windings 1941 S. two about or contact in opposing surface of the adjacent and opposing winding 1941. Convex bumps 1949 serve as spacers between the windings, providing a volume in which gas or air is retained or captured to facilitate the regulation of the rate at which therapeutics 1250 are diffused or otherwise released from delivery device 1920.

As shown by FIG. 42, bumps 1949 may extend from one or both of the opposite faces of each of the windings or from one or both of the opposite faces of sheet 1940. For example, bumps 1949A in 1949B project from only one side of windings 1941B and 1941C, respectively, on one side 1951 of sheet 1940. Bump 1949E projects from only one side of winding 1941F, on side 1953 of sheet 1940. Bumps 1949C and 1949D as well as bumps 1949F and 1949G extend from opposite sides of windings 1941D and 1941F, respectively. To regulate the rate at which therapeutic masses 1250 are diffused or otherwise released from within the various windings 1941, the height, shape, width, density and distribution of such bumps 1949 are varied along each winding 1941 and radially from winding to winding.

In the example illustrated, sheet 1940 is illustrated as including therapeutics in the form of therapeutic masses 1250B and 1250C (described above). Sheet 1940 is further illustrated as comprising perforations 1441 (described above). In other implementations, sheet 1940 includes therapeutics in the form of therapeutic masses 1250A, 1250B, 1250C or various combinations of masses 1250A-1250C. In other implementations, sheet 1940 may omit perforations 1441.

Figure 43:
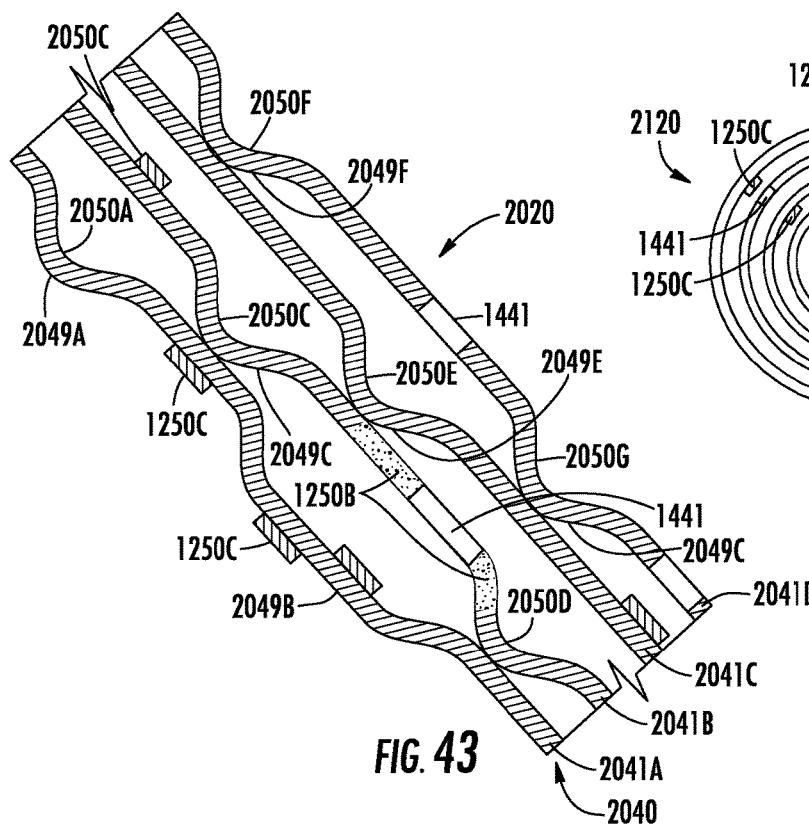
FIG. 43 is a fragmentary sectional view of a portion of another example therapeutic delivery device.

FIG. 43 is a sectional view illustrating a portion of therapeutic delivery device 2020, another implementation of therapeutic delivery device 1220. Therapeutic delivery device 2020 comprises one or more sheets 2040 wound to form a plurality of windings. FIG. 43 illustrates four of such windings 2041A, 2041B, 2041C, 2041D, (collectively referred to as windings 2041). In the example illustrated, such windings 2041 are formed by the winding of a single sheet 2040. In other implementations, such windings 2041 may be formed by a plurality of such sheets 2040.

As shown by FIG. 43, sheet 2040 is wavy or undulates so as to form a plurality of convex bumps 2049A, 2049B, 2049C, 2049D, 2049E, 2049F and 2040G (collectively referred to as convex bumps 2049) and a corresponding plurality of concave depressions 2050A, 2050B, 2050C, 2050D, 2050E, 2050F and 2050G (collectively referred to as concave depressions 2050). Each of convex bumps 2049 extend opposite to a corresponding associated concave depression 2050. In other words, each convex bump 2049 extends on one side of its winding 2041 with an opposite concave depression extending on a directly opposite side of the same winding 2041.

As shown by FIG. 43, convex bumps 2049 abut, contact and engage the service of the adjacent and opposing winding 2041 on opposite sides of an intermediate concave depression 2050. As a result, convex bumps 2049 at least partially seal about the intermediate concave depression 2052 caption retain and air or gas within the thus formed pocket, wherein the air or gas regulates the subsequent degradation of delivery device 2020 and the diffusion of therapeutics from delivery device 2020. Convex bumps 2049 further serve as spacers adjacent windings from one another for the retention of air or gas. To regulate the rate at which therapeutic masses 1250 are diffused or otherwise released from within the various windings 2041, the height, shape, width, density and distribution of such undulations or waves forming bumps 2049 and their corresponding depressions 2050 are varied along each winding 2041 and radially from winding to winding.

In the example illustrated, sheet 2040 is illustrated as including therapeutics in the form of therapeutic masses 1250B and 1250C (described above). Sheet 2040 is further illustrated as comprising perforations 1441 (described above). In other implementations, sheet 2040 includes therapeutics in the form of therapeutic masses 1250A, 1250B, 1250C or various combinations of masses 1250A-1250C. In other implementations, sheet 2040 may omit perforations 1441.

Figure 44:
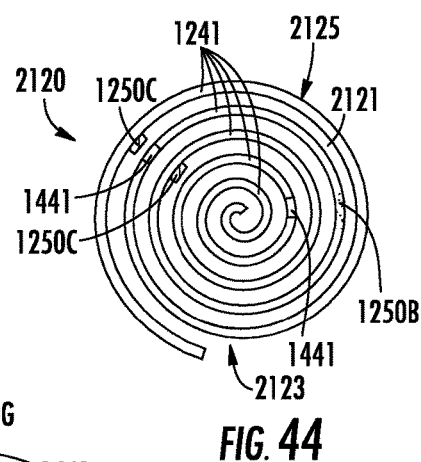
FIG. 44 is a sectional view of another example therapeutic delivery device.

In each of the above examples, the various sheets are illustrated as being concentrically wound about a centerline or central axis. In other implementations, each of the various sheets are alternatively not concentric or off-centered. FIG. 44 is a sectional view illustrating therapeutic delivery device 2120 formed from sheet 1240 having windings 1241 which are not concentric, but which are off centered relative to one another. The non-concentric winding of sheet 1240 results in portions of each winding 1241 being extremely close to one another or in contact with one another with other portions of the same windings 1241 being spaced from one another to form air or gas containing volumes or spaces 2121. Those portions of each winding 1241 that contact one another such as at side portion 2123, assist in reducing the likelihood that such windings will unwind and assists in retaining the nonconcentric shape or arrangement of such windings 1241. In one implementation, windings 1241 inside portion 2123 stick to one another to assist in maintaining the spacing between windings 1241 alongside portion 2125. Although therapeutic device 2120 is illustrated as being formed from sheet 1240 wound in a nonconcentric fashion, in other implementations, sheet 1240 may additionally be folded (as shown in FIG. 31) prior to being wound in a nonconcentric fashion. In yet other implementations, therapeutic device 2120 is formed from alternative implementations of sheet 1240, such as sheet 1840, sheet 1940 or sheet 2040. In other implementations, therapeutic device 2120 is formed from multiple sheets which are wound in a nonconcentric fashion. In the example illustrated, sheet 2140 is illustrated as including therapeutics in the form of therapeutic masses 1250B and 1250C (described above). Sheet 2040 is further illustrated as comprising perforations 1441 (described above). In other implementations, sheet 2140 includes therapeutics in the form of therapeutic masses 1250A, 1250B, 1250C or various combinations of masses 1250A-1250C. In other implementations, sheet 2140 may omit perforations 1441.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A therapeutic delivery device taken orally or via implant comprising:
    a layer of biodegradable material wound into a plurality of windings, the plurality of windings comprising an outermost winding defining an internal volume and winding pairs including a first winding pair and a second winding pair, wherein the layer comprises a folded layer, the folded layer being wound into the plurality of windings;
    a first therapeutic mass incorporated in or on the layer along the first winding pair;
    a second therapeutic mass incorporated in or on the layer along the second winding pair; and
    at least one volume of gas captured within the internal volume and occupying at least 50% of the internal volume.

2. The therapeutic delivery device of claim 1, wherein the layer comprises a side having convex bumps spacing the windings of one of the winding pairs.

3. The therapeutic delivery device of claim 1, wherein the windings are eccentrically wound.

4. The therapeutic delivery device of claim 1, wherein the layer has a varying thickness, wherein thinner portions of the layer form voids containing the at least one volume of gas.

5. The therapeutic delivery device of claim 4, wherein the layer comprises grooves along the thinner portions of the layer.

6. The therapeutic delivery device of claim 1 further comprising an outer shell about the windings.

7. The therapeutic delivery device of claim 1, wherein the at least one volume of gas has density that varies radially amongst the winding pairs along the internal volume.

8. The therapeutic delivery device of claim 1, wherein the at least one volume of gas has a density that varies circumferentially along at least one of the winding pairs.

9. The therapeutic delivery device of claim 1, wherein the layer has a first face and a second opposite face, wherein a first portion of the first face is directly opposite a second portion of the first face upon being folded with a gap linearly extending from the first portion to the second portion and wherein the folded layer is wound so as to spiral about an axis.

10. The therapeutic delivery device of claim 1, wherein the layer has a bent U-shaped portion along a fold line of the layer and wherein the folded layer spirally winds about an axis.

11. The therapeutic delivery device of claim 4, wherein the layer is nonporous.

12. A therapeutic delivery device taken orally or via implant comprising:
    a layer of biodegradable material wound into a plurality of windings, the plurality of windings comprising an outermost winding defining an internal volume and winding pairs including a first winding pair and a second winding pair;
    a first therapeutic mass incorporated in or on the layer along the first winding pair;
    a second therapeutic mass incorporated in or on the layer along the second winding pair;
    at least one volume of gas captured within the internal volume and occupying at least 50% of the internal volume; and
    a spacer between the windings to form pockets containing the at least one volume of gas.

13. The therapeutic delivery device of claim 12, wherein the spacer comprises a grid.

14. The therapeutic delivery device of claim 12, wherein the spacer comprises posts projecting from the layer.

15. A therapeutic delivery device taken orally or via implant comprising:
    a layer of biodegradable material wound into a plurality of windings, the plurality of windings comprising an outermost winding defining an internal volume and winding pairs including a first winding pair and a second winding pair, wherein the layer comprises a first side having concave depressions containing the at least one volume of gas;
    a first therapeutic mass incorporated in or on the layer along the first winding pair;
    a second therapeutic mass incorporated in or on the layer along the second winding pair;
    at least one volume of gas captured within the internal volume and occupying at least 50% of the internal volume, wherein the layer comprises a second side opposite the first side, the second side having convex bumps corresponding to and opposite the concave depressions, wherein the concave depressions and the convex bumps of adjacent winding pairs are offset.

16. The therapeutic delivery device of claim 15, wherein the layer is undulating on the first side and the second side so as to form the convex bumps corresponding to and opposite the concave depressions.

17. A therapeutic delivery device taken orally or via implant comprising:
- a layer of biodegradable material wound into a plurality of windings, the plurality of windings comprising an outermost winding defining an internal volume and winding pairs including a first winding pair and a second winding pair;
- a first therapeutic mass incorporated in or on the layer along the first winding pair;
- a second therapeutic mass incorporated in or on the layer along the second winding pair;
- at least one volume of gas captured within the internal volume and occupying at least 50% of the internal volume, wherein the windings are eccentrically wound.

18. A therapeutic delivery device taken orally or via implant comprising:
- a layer of biodegradable material wound into a plurality of windings, the plurality of windings comprising an outermost winding defining an internal volume and winding pairs including a first winding pair and a second winding pair;
- a first therapeutic mass incorporated in or on the layer along the first winding pair;
- a second therapeutic mass incorporated in or on the layer along the second winding pair;
- at least one volume of gas captured within the internal volume and occupying at least 50% of the internal volume, wherein the at least one volume of gas has a density that varies circumferentially along at least one of the winding pairs.

19. The therapeutic delivery device of claim 18, wherein the at least one volume of gas has density that varies radially amongst the winding pairs along the internal volume.

* * * * *